(12) United States Patent
Ehrenfreund et al.

(10) Patent No.: US 7,994,093 B2
(45) Date of Patent: *Aug. 9, 2011

(54) HETEROCYCLOCARBOXAMIDE DERIVATIVES

(75) Inventors: Josef Ehrenfreund, Basel (CH); Hans Tobler, Basel (CH); Harald Walter, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/549,478

(22) Filed: Aug. 28, 2009

(65) Prior Publication Data

US 2010/0010063 A1 Jan. 14, 2010

Related U.S. Application Data

(63) Continuation of application No. 10/530,737, filed as application No. PCT/EP03/11388 on Oct. 14, 2003, now Pat. No. 7,598,395.

(30) Foreign Application Priority Data

Oct. 18, 2002 (GB) .................................. 0224316.0
Oct. 14, 2003 (WO) ...................... PCT/EP03/11388

(51) Int. Cl.

| A01N 43/40 | (2006.01) |
|---|---|
| A01N 43/72 | (2006.01) |
| A01N 43/60 | (2006.01) |
| A01N 43/36 | (2006.01) |
| A01N 43/00 | (2006.01) |
| A01N 43/02 | (2006.01) |
| C07D 239/02 | (2006.01) |
| C07D 241/02 | (2006.01) |
| C07D 213/46 | (2006.01) |
| C07D 207/00 | (2006.01) |
| C07D 335/02 | (2006.01) |
| C07D 333/32 | (2006.01) |
| C07D 333/34 | (2006.01) |
| C07D 315/00 | (2006.01) |
| C07D 307/02 | (2006.01) |

(52) U.S. Cl. ........ 504/130; 504/131; 504/136; 504/138; 504/139; 504/140; 544/335; 544/406; 546/314; 546/329; 548/537; 549/28; 549/64; 549/425; 549/487

(58) Field of Classification Search .................. 504/221, 504/223, 227, 235, 244, 261, 283, 288, 291, 504/130, 131, 136, 138, 139, 140; 564/189, 564/191; 544/335, 406; 546/314, 329; 548/537; 549/28, 64, 425, 487

See application file for complete search history.

(56) References Cited

U.S. PATENT DOCUMENTS

| 2,950,308 A | 8/1960 | Dunbar |
| 3,375,275 A | 3/1968 | Dunbar |
| 4,742,074 A | 5/1988 | Nishida et al. |
| 5,093,347 A | 3/1992 | Graneto et al. |
| 5,675,016 A | 10/1997 | Gallenkamp et al. |
| 6,365,620 B2 | 4/2002 | Eberle et al. |

FOREIGN PATENT DOCUMENTS

| EP | 0256503 | 2/1988 |
| EP | 0276177 | 7/1988 |
| EP | 0280275 | 8/1988 |
| EP | 0315502 | 8/1988 |
| EP | 0368749 | 5/1990 |
| EP | 0654464 | 5/1995 |
| JP | 62249966 | 10/1987 |
| JP | 1117864 | 3/1989 |
| JP | 1070479 | 11/1989 |
| JP | 1275574 | 11/1989 |

(Continued)

OTHER PUBLICATIONS

M. Oda et al., Structure Activity Relationships of N-(1,1,3-Trimethylindan-4-yl) Carboxamide Fungicides, J. Pesticide Sci, 1993, vol. 18, No. 3 pp. 245-251.

(Continued)

*Primary Examiner* — Sreeni Padmanabhan
*Assistant Examiner* — Sarah Pihonak
(74) *Attorney, Agent, or Firm* — Rebecca Howard

(57) ABSTRACT

The invention relates to a fungicidally active compound of formula (I):

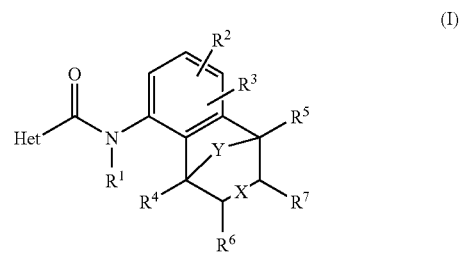

where Het is a 5- or 6-membered heterocyclic ring containing one to three heteroatoms, each independently selected from oxygen, nitrogen and sulphur, provided that the ring is not 1,2,3-triazole, the ring being substituted by groups $R^8$, $R^9$ and $R^{10}$; X is a single or double bond; Y is O, S, $N(R^{11})$ or $(CR^{12}R^{13})(CR^{14}R^{15})_m(CR^{16}R^{17})_n$; m is 0 or 1; n is 0 or 1; and $R^1$ to $R^{17}$ each, independently, have a range of values; to the preparation of these compounds, to novel intermediates used in the preparation of these compounds, to agrochemical compositions which comprise at least one of the novel compounds as active ingredient, to the preparation of the compositions mentioned and to the use of the active ingredients or compositions in agriculture or horticulture for controlling or preventing infestation of plants by phytopathogenic microorganisms, preferably fungi.

20 Claims, No Drawings

FOREIGN PATENT DOCUMENTS

| | | |
|---|---|---|
| JP | 1313402 | 12/1989 |
| JP | 2157366 | 2/1992 |
| JP | 4054173 | 2/1992 |
| JP | 2040374 | 2/1998 |
| JP | 2040384 | 2/1999 |
| WO | 9212970 | 8/1992 |
| WO | 02059086 | 8/2002 |

OTHER PUBLICATIONS

Grave et al. "Photochemistry of the o-nitrobenzyl system in solution: effects of O•••H distance and geometrical constraint of the hydrogen transfer mechanism in the excited state," Canadian Journal of Chemistry, vol. 69, pp. 1193-1200 (1991).

A.J. Kirby et al.: "Efficiency of Proton Tranfer Catalysis, Intramolecular General Acid Catalysis of the Hydrolysis of Dialkyl Acetals of Benzaldehyde," J. Chemical Society, Perkin Transactions, No. 2, 1997, pp. 1081-1093.

Oda, Masatsugu et al.: "Quantitative Structure activity relationship of 2-chloropyridine-3-carboxamine Fungicides," Journal of Pesticide Science (Int. ed.), No. 18, 1992, pp. 49-57.

Database Crossfire Beilstein Online No. XP-002271778, Beilstein Registry No. 7269102, (1996).

Snow, Robert A., et al., "Demostration and Analysis of bridging regioselectively operative during di-pi,-methane . . . ", Journal American Chem. Soceity, vol. 99, No. 11, 1977, pp. 3734-3744.

HETEROCYCLOCARBOXAMIDE DERIVATIVES

This application is a continuation application of U.S. Ser. No. 10/530,737, filed Apr. 8, 2005, still pending, which is a 371 of International Application No. PCT/EP03/011388 filed Oct. 14, 2003, which claims priority to GB 0224316.0 filed Oct. 18, 2002, the contents of which are incorporated herein by reference.

The present invention relates to novel tricyclic amine derivatives which have microbiocidal activity, in particular fungicidal activity. The invention also relates to the preparation of these compounds, to novel intermediates used in the preparation of these compounds, to agrochemical compositions which comprise at least one of the novel compounds as active ingredient, to the preparation of the compositions mentioned and to the use of the active ingredients or compositions in agriculture or horticulture for controlling or preventing infestation of plants by phytopathogenic microorganisms, preferably fungi.

The present invention provides a compound of formula (I):

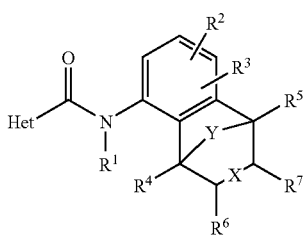

where Het is a 5- or 6-membered heterocyclic ring containing one to three heteroatoms, each independently selected from oxygen, nitrogen and sulphur, provided that the ring is not 1,2,3-triazole, the ring being substituted by groups $R^8$, $R^9$ and $R^{10}$; X is a single or double bond; Y is O, S, $N(R^{11})$ or $(CR^{12}R^{13})(CR^{14}R^{15})_m(CR^{16}R^{17})_n$; m is 0 or 1; n is 0 or 1; $R^1$ is hydrogen, $C_{1-4}$ alkyl, $C_{1-4}$ haloalkyl, $C_{1-4}$ alkoxy, $C_{1-4}$ haloalkoxy, $CH_2C\equiv CR^{18}$, $CH_2CR^{19}=CHR^{20}$, $CH=C=CH_2$ or $COR^{21}$; $R^2$ and $R^3$ are each, independently, hydrogen, halogen, $C_{1-4}$ alkyl, $C_{1-4}$ alkoxy or $C_{1-4}$ haloalkoxy; $R^4$, $R^5$, $R^6$ and $R^7$ are each, independently, hydrogen, halogen, $C_{1-4}$ alkyl, $C_{1-4}$ haloalkyl, $C_{1-4}$ alkoxy, $C_{1-4}$ haloalkoxy, $C_{1-4}$ alkylthio, $C_{1-4}$ haloalkylthio, hydroxymethyl, $C_{1-4}$ alkoxymethyl, $C(O)CH_3$ or $C(O)OCH_3$; $R^8$, $R^9$ and $R^{10}$ are each, independently, hydrogen, halogen, cyano, nitro, $C_{1-4}$ alkyl, $C_{1-4}$ haloalkyl, $C_{1-4}$ alkoxy($C_{1-4}$)alkylene or $C_{1-4}$ haloalkoxy($C_{1-4}$)alkylene, provided that at least one of $R^8$, $R^9$ and $R^{10}$ is not hydrogen; $R^{11}$ is hydrogen, $C_{1-4}$ alkyl, benzyl (in which the phenyl group is optionally substituted with up to three substituents, each independently selected from halogen, $C_{1-4}$ alkyl, $C_{1-4}$ haloalkyl and $C_{1-4}$ alkoxy), formyl, $C(O)C_{1-4}$ alkyl (optionally substituted by halogen or $C_{1-4}$ alkoxy), $C(=O)O-C_{1-6}$ alkyl (optionally substituted by halogen, $C_{1-4}$ alkoxy or cyano) or $C_{1-4}$ alkoxy($C_{1-4}$)alkylene; $R^{12}$, $R^{13}$, $R^{14}$, $R^{15}$, $R^{16}$ and $R^{17}$ are each, independently, hydrogen, halogen, hydroxy, $C_{1-6}$ alkyl, $C_{2-6}$ alkenyl [both optionally substituted by halogen, hydroxy, $C_{1-4}$ alkoxy, =O, aryl or $O-C(O)-C_{1-4}$ alkyl or a 3-7 membered carboxylic ring (itself optionally substituted by up to three methyl groups)], a 3-7 membered saturated ring (optionally substituted by up to three methyl groups and optionally containing one heteroatom selected from nitrogen and oxygen) or $C_{1-4}$ alkoxy; or $R^{12}$ and $R^{13}$ together with the carbon atom to which they are attached form the group C=O or a 3-5 membered carbocyclic ring (optionally substituted by up to three methyl groups and optionally with up to 2 heteroatoms each independently selected from O and N); or $R^{12}$ and $R^{13}$ together form a $C_{1-6}$ alkylidene (optionally substituted by up to three methyl groups) or a $C_{3-6}$ cycloalkylidene group (optionally substituted by up to three methyl groups); $R^{18}$, $R^{19}$ and $R^{20}$ are each, independently, hydrogen, halogen, $C_{1-4}$ alkyl, $C_{1-4}$ haloalkyl or $C_{1-4}$ alkoxy($C_{1-4}$)alkylene; and $R^{21}$ is hydrogen, $C_{1-6}$ alkyl, $C_{1-6}$ haloalkyl, $C_{1-4}$ alkoxy($C_{1-4}$)alkylene, $C_{1-4}$ alkyl-S—$(C_{1-4})$alkylene, $C_{1-4}$ alkoxy or aryl.

Halogen is fluoro, chloro, bromo or iodo; preferably fluoro, chloro or bromo.

Each alkyl moiety is a straight or branched chain and is, for example, methyl, ethyl, n-propyl, n-butyl, n-pentyl, n-hexyl, iso-propyl, sec-butyl, iso-butyl, tert-butyl, neo-pentyl, n-heptyl, 1,3-dimethylbutyl, 1,3-dimethylpentyl, 1-methyl-3-ethyl-butyl or 1,3,3-trimethylbutyl. Likewise, each alkylene moiety is a straight or branched chain.

Haloalkyl moieties are alkyl moieties which are substituted by one or more of the same or different halogen atoms and are, for example, $CF_3$, $CF_2Cl$, $CHF_2$, $CH_2F$, $CCl_3$, $CF_3CH_2$, $CHF_2CH_2$, $CH_2FCH_2$, $CH_3CHF$ or $CH_3CF_2$.

Alkenyl and alkynyl moieties can be in the form of straight or branched chains.

Each alkenyl moiety, where appropriate, may be of either the (E)- or (Z)-configuration.

A 3-5 membered carbocyclic ring includes a spiro-three or five membered ring.

Aryl includes phenyl, naphthyl, anthracyl, fluorenyl and indanyl but is preferably phenyl.

Alkylidene moieties may be in the form of straight or branched chains. Alkylidene includes methylidene [$CH_2=$], ethylidene [$CH_3C(H)=$], n-propylidene, i-propylidene [$(CH_3)_2C=$], n-butylidene, i-butylidene, 2-butylidene, n-pentylidene, i-pentylidene, neo-pentylidene, 2-pentylidene, n-hexylidene, 2-hexylidene, 3-hexylidene, i-hexylidene and neo-hexylidene.

Cycloalkyl includes cyclopropyl, cyclobutyl, cyclopentyl, cyclohexyl, cycloheptyl and cyclooctyl.

Cycloalkenyl includes cyclobutenyl, cyclopentenyl, cyclohexenyl and cycloheptenyl.

Cycloalkylidene includes cyclopropylidene [$c(C_3H_4)=$], cyclobutylidene, cyclopentylidene and cyclohexylidene.

In one aspect of the invention, $R^{11}$ is hydrogen, $C_{1-4}$ alkyl, benzyl (in which the phenyl group is optionally substituted with up to three substituents, each independently selected from halogen, $C_{1-4}$ alkyl, $C_{1-4}$ haloalkyl and $C_{1-4}$ alkoxy), formyl, $C(O)C_{1-4}$ alkyl or $C_{1-4}$ alkoxy($C_{1-4}$)alkylene.

In another aspect of the invention, $R^{12}$, $R^{13}$, $R^{14}R^{15}$, $R^{16}$ and $R^{17}$ are each, independently, hydrogen, $C_{1-4}$ alkyl or $C_{1-4}$ alkoxy.

Het is preferably pyrrolyl, pyrazolyl, thiazolyl, oxazolyl, pyridinyl, pyrimidyl, pyridazinyl, 2,3-dihydro-[1,4]oxathiine-6-yl, oxazinyl, thiazinyl or triazinyl.

Het is more preferably pyrrolyl, pyrazolyl, thiazolyl, oxazolyl, pyridinyl or 2,3-dihydro-[1,4]oxathiine-yl.

Het is even more preferably pyrrolyl, pyrazolyl, thiazolyl or pyridinyl.

Het is most preferably pyrrolyl or pyrazolyl.

Preferably X is a single bond.

In one aspect, Y is O, S, $N(R^{11})$, $CH_2$, $CH_2CH_2$, $CH_2CH_2CH_2$, $C(CH_3)_2$, $CH(CH_3)$, $CH(C_2H_5)$, $C(CH_3)(C_2H_5)$, $CH(OCH_3)$ or $C(OCH_3)_2$; more preferably $N(R^{11})$, O, S, $CH_2$, $CH_2CH_2$, $CH_2CH_2CH_2$, $C(CH_3)_2$, $CH(CH_3)$ or $CH(C_2H_5)$; even more preferably $N(R^{11})$, O, S, $CH_2$ or $CH_2CH_2$; and still more preferably O, $CH_2$ or $N(R^{11})$.

Preferably Y is O, N($R^{11}$) or $(CR^{12}R^{13})(CR^{14}R^{15})_m(CR^{16}R^{17})_n$.

More preferably Y is O or $(CR^{12}R^{13})(CR^{14}R^{15})_m(CR^{16}R^{17})_n$.

Even more preferably Y is $(CR^{12}R^{13})(CR^{14}R^{15})_m(CR^{16}R^{17})_n$.

Still more preferably Y is $(CR^{12}R^{13})$.

Preferably n is 0.

Preferably m is 0.

Preferably $R^1$ is hydrogen, $CH_2C\equiv CR^{18}$, $CH=C=CH_2$ or $COR^{21}$.

More preferably $R^1$ is hydrogen, $CH_2C\equiv CH$, $CH=C=CH_2$, C(O)H or $C(O)CH_3$.

Yet more preferably $R^1$ is hydrogen, $CH_2C\equiv CH$, $CH=C=CH_2$ or $C(O)CH_3$.

Even more preferably $R^1$ is hydrogen, $CH_2C\equiv CH$ or $CH=C=CH_2$.

Most preferably $R^1$ is hydrogen.

Preferably $R^2$ is hydrogen, halogen or $C_{1-4}$ alkyl.

More preferably $R^2$ is hydrogen or halogen.

Most preferably $R^2$ is hydrogen.

Preferably $R^3$ is hydrogen or methyl.

More preferably $R^3$ is hydrogen.

Preferably $R^4$ is hydrogen, $C_{1-4}$ alkyl, halogen, $C_{1-4}$ haloalkyl, $C_{1-4}$ alkoxy, $C(O)CH_3$ or $C(O)OCH_3$.

More preferably $R^4$ is hydrogen, $C_{1-2}$ alkyl, halogen, $CF_3$, methoxy, $C(O)CH_3$ or $C(O)OCH_3$.

Even more preferably $R^4$ is hydrogen, methyl, chlorine, $CF_3$ or methoxy.

Most preferably $R^4$ is hydrogen or methyl.

Preferably $R^5$ is hydrogen, $C_{1-4}$ alkyl, halogen, $C_{1-4}$ haloalkyl, $C_{1-4}$ alkoxy, $C(O)CH_3$ or $C(O)OCH_3$.

More preferably $R^5$ is hydrogen, $C_{1-2}$ alkyl, chlorine, $CF_3$, methoxy, $C(O)CH_3$ or $C(O)OCH_3$.

Most preferably $R^5$ is hydrogen or methyl.

Preferably $R^6$ is hydrogen, $C_{1-4}$ alkyl, $C_{1-4}$ alkoxy or $C(O)CH_3$.

More preferably $R^6$ is hydrogen, methyl, methoxy or $C(O)CH_3$.

Most preferably $R^6$ is hydrogen or methyl.

Preferably $R^7$ is hydrogen, $C_{1-4}$ alkyl, $C_{1-4}$ alkoxy or $C(O)CH_3$.

More preferably $R^7$ is hydrogen, methyl, methoxy or $C(O)CH_3$.

Most preferably $R^7$ is hydrogen or methyl.

Preferably $R^8$ is hydrogen, halogen, $C_{1-4}$ alkyl, $C_{1-4}$ haloalkyl or methoxymethylene.

More preferably $R^8$ is hydrogen, chloro, fluoro, bromo, $C_{1-2}$ alkyl, $CF_3$, $CF_2Cl$, $CHF_2$, $CH_2F$ or methoxymethylene.

Even more preferably $R^8$ is hydrogen, chloro, fluoro, $C_{1-2}$ alkyl, $CF_3$, $CF_2Cl$, $CHF_2$, $CH_2F$ or methoxymethylene.

Most preferably $R^8$ is hydrogen, chloro, fluoro, methyl, $CF_3$, $CHF_2$ or $CH_2F$.

Preferably $R^9$ is hydrogen, halogen, $C_{1-4}$ alkyl or $C_{1-4}$ haloalkyl or methoxymethylene.

More preferably $R^9$ is hydrogen, chloro, fluoro, bromo, $C_{1-2}$ alkyl, $CF_3$, $CF_2Cl$, $CHF_2$, $CH_2F$ or methoxymethylene.

Even more preferably $R^9$ is hydrogen, chloro, fluoro, $C_{1-2}$ alkyl, $CF_3$, $CF_2Cl$, $CHF_2$, $CH_2F$ or methoxymethylene.

Most preferably $R^9$ is hydrogen, chloro, fluoro, methyl, $CF_3$, $CHF_2$ or $CH_2F$.

Preferably $R^{10}$ is hydrogen, halogen, $C_{1-4}$ alkyl, $C_{1-4}$ haloalkyl or methoxymethylene.

More preferably $R^{10}$ is hydrogen, chloro, fluoro, bromo, $C_{1-2}$ alkyl, $CF_3$, $CF_2Cl$, $CHF_2$, $CH_2F$ or methoxymethylene.

Even more preferably $R^{10}$ is hydrogen, chloro, fluoro, $C_{1-2}$ alkyl, $CF_3$, $CF_2Cl$, $CHF_2$, $CH_2F$ or methoxymethylene.

Most preferably $R^{10}$ is hydrogen, chloro, fluoro, methyl, $CF_3$, $CHF_2$ or $CH_2F$.

In one aspect of the invention $R^{11}$ is hydrogen, $C_{1-4}$ alkyl, benzyl, formyl, $C(O)CH_3$ or $C(O)OC(CH_3)_3$; more preferably hydrogen or $C_{1-2}$ alkyl.

Preferably $R^{11}$ is $C_{1-4}$ alkyl, formyl, $C(O)CH_3$ or $C(O)OC_{1-6}$ alkyl (optionally substituted by halogen, CN or $C_{1-4}$ alkoxy).

More preferably $R^{11}$ is $C(O)OC_{1-4}$ alkyl.

In one aspect of the invention $R^{12}$, $R^{13}$, $R^{14}$, $R^{15}$, $R^{16}$ and $R^{17}$ are each, independently, hydrogen, $C_{1-2}$ alkyl or methoxy.

Preferably $R^{12}$ and $R^{13}$ are each, independently, hydrogen, halogen, $C_{1-5}$ alkyl, $C_{1-3}$ alkoxy, $CH_2OH$, CH(O), $C_{3-6}$ cycloalkyl, $CH_2O—C(=O)CH_3$, $CH_2—C_{3-6}$ cycloalkyl or benzyl; or $R^{12}$ and $R^{13}$ together with the carbon atom to which they are attached form the group C=O or a 3-5 membered carbocyclic ring; or $R^{12}$ and $R^{13}$ together form $C_{1-5}$ alkylidene or $C_{3-6}$ cycloalkylidene.

More preferably $R^{12}$ and $R^{13}$ are, independently, H, $CH_3$, $C_2H_5$, n-$C_3H_7$, i-$C_3H_7$, n-$C_4H_9$, sec-$C_4H_9$, i-$C_4H_9$, $CH(C_2H_5)_2$, $CH_2$-cyclopropyl or cyclopentyl; or $R^{12}$ and $R^{13}$ together with the carbon atom to which they are attached form a 3-membered or 5-membered carbocyclic ring.

Preferably $R^{14}$ is H or $CH_3$.

Preferably $R^{15}$ is H or $CH_3$.

Preferably $R^{16}$ is H or $CH_3$.

Preferably $R^{17}$ is H or $CH_3$.

Preferably $R^{18}$ is hydrogen, chloro, bromo, methyl or methoxy.

More preferably $R^{18}$ is hydrogen, chloro or methyl.

Most preferably $R^{18}$ is hydrogen.

Preferably $R^{19}$ is hydrogen, chloro, bromo, methyl or methoxy.

More preferably $R^{19}$ is hydrogen, chloro or methyl.

Most preferably $R^{19}$ is hydrogen.

Preferably $R^{20}$ is hydrogen, chloro, bromo, methyl or methoxy.

More preferably $R^{20}$ is hydrogen, chloro or methyl.

Most preferably $R^{20}$ is hydrogen.

Preferably $R^{21}$ is hydrogen, methyl, $OC(CH_3)_3$ or $CH_3OCH_2$.

Compounds of formula (C):

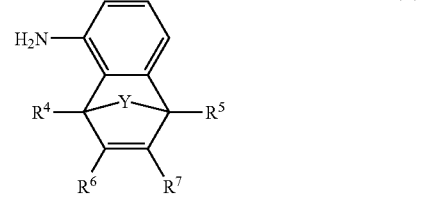

(C)

where Y, $R^4$, $R^5$, $R^6$ and $R^7$ are as defined above for a compound of formula (I) are useful as intermediates in the preparation of compounds of formula (I). Some Compounds of formula (C) are novel but some are already known.

Therefore, in another aspect, the present invention provides a compound of formula (C) where Y is O or S; and $R^4$, $R^5$, $R^6$ and $R^7$ are each $C(O)OCH_3$; or Y is N($R^{11}$) or $(CR^{12}R^{13})(CR^{14}R^{15})_m(CR^{16}R^{17})_n$; $R^4$, $R^5$, $R^6$, $R^7$, $R^{14}$, $R^{15}$, $R^{16}$, $R^{17}$, m and n are each as defined above for a compound of formula (I); $R^{11}$ is benzyl (in which the phenyl group is optionally substituted with up to three substituents, each independently selected from halogen, $C_{1-4}$ alkyl, $C_{1-4}$ haloalkyl and $C_{1-4}$ alkoxy); and $R^{12}$ and $R^{13}$ together with the carbon atom to which they are attached form a 3-5 membered carbocyclic ring (optionally substituted by up to three methyl groups and containing 1 or 2 heteroatoms each independently selected from O and N).

Compounds of formula (D):

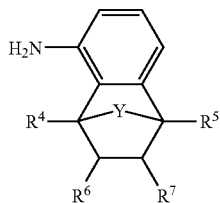

where Y, $R^4$, $R^5$, $R^6$ and $R^7$ are as defined above for a compound of formula (I) are also useful as intermediates in the preparation of compounds of formula (I). Some Compounds of formula (D) are novel but some are already known.

Therefore, in another aspect, the present invention provides a compound of formula (D) where Y is O or S; and $R^4$, $R^5$, $R^6$ and $R^7$ are each $C(O)OCH_3$; or Y is $N(R^{11})$ or $(CR^{12}R^{13})(CR^{14}R^{15})_m(CR^{16}R^{17})_n$; $R^4$, $R^5$, $R^6$, $R^7$, $R^{14}$, $R^{15}$, $R^{16}$, $R^{17}$, m and n are each as defined above for a compound of formula (I); $R^{11}$ is benzyl (in which the phenyl group is optionally substituted with up to three substituents, each independently selected from halogen, $C_{1-4}$ alkyl, $C_{1-4}$ haloalkyl and $C_{1-4}$ alkoxy); and $R^{12}$ and $R^{13}$ together with the carbon atom to which they are attached form a 3-5 membered carbocyclic ring (optionally substituted by up to three methyl groups and containing 1 or 2 heteroatoms each independently selected from O and N).

The compounds of formula (I), (C) and (D) may exist as different geometric or optical isomers or in different tautomeric forms. This invention covers, for each formula, all such isomers and tautomers and mixtures thereof in all proportions as well as isotopic forms such as deuterated compounds.

The compounds in Tables 1 to 29 below illustrate compounds of the invention.

Table 1 provides 94 compounds of formula (C) wherein Y, $R^4$, $R^5$, $R^6$ and $R^7$ are as defined in Table 1.

TABLE 1

| Compound Number | $R^4$ | $R^5$ | $R^6$ | $R^7$ | Y |
|---|---|---|---|---|---|
| 1.01 | $CH_3$ | $CH_3$ | H | H | O |
| 1.02 | $CH_3$ | H | H | H | O |
| 1.03 | H | $CH_3$ | H | H | O |
| 1.04 | $CH_3$ | $CH_3$ | $C(O)CH_3$ | H | O |
| 1.05 | $CH_3$ | $CH_3$ | H | $C(O)CH_3$ | O |
| 1.06 | $CH_3$ | $C(O)CH_3$ | H | H | O |
| 1.07 | $C(O)CH_3$ | $CH_3$ | H | H | O |
| 1.08 | $C(O)OCH_3$ | H | H | H | O |
| 1.09 | H | $C(O)OCH_3$ | H | H | O |
| 1.10 | H | H | H | H | O |
| 1.11 | $CF_3$ | $CF_3$ | H | H | O |
| 1.12 | $OCH_3$ | $OCH_3$ | H | H | O |
| 1.13 | H | H | $CH_3$ | $CH_3$ | O |
| 1.14 | $C_2H_5$ | $C_2H_5$ | H | H | O |
| 1.15 | CH3 | H | $CH_3$ | H | O |
| 1.16 | H | CH3 | H | $CH_3$ | O |
| 1.17 | $CH_3$ | H | $CH_3$ | H | $CH_2$ |
| 1.18 | H | $CH_3$ | H | $CH_3$ | $CH_2$ |
| 1.19 | $CH_3$ | $CH_3$ | $CH_3$ | $CH_3$ | $CH_2$ |
| 1.20 | $CH_3$ | $CH_3$ | $CH_3$ | $CH_3$ | $CH(CH_3)$ |
| 1.21 | H | H | H | H | $CH(CH_3)$ |
| 1.22 | $CH_3$ | $CH_3$ | H | H | $CH_2CH_2$ |
| 1.23 | H | H | $CH_3$ | $CH_3$ | $CH_2CH_2$ |
| 1.24 | H | H | H | H | $CH_2CH_2CH_2$ |
| 1.25 | H | H | $CH_3$ | $CH_3$ | $C(CH_3)_2$ |
| 1.26 | $CH_3$ | $CH_3$ | $CH_3$ | $CH_3$ | $C(CH_3)_2$ |
| 1.27 | $CH_3$ | H | $CH_3$ | H | $C(CH_3)_2$ |
| 1.28 | H | $CH_3$ | H | $CH_3$ | $C(CH_3)_2$ |
| 1.29 | H | H | H | H | $C(CH_3)_2$ |
| 1.30 | $CH_3$ | $CH_3$ | H | H | $C(CH_3)_2$ |
| 1.31 | H | H | H | H | $C(OCH_3)_2$ |
| 1.32 | H | H | H | H | S |
| 1.33 | $CH_3$ | $CH_3$ | H | H | S |
| 1.34 | H | H | $CH_3$ | $CH_3$ | S |
| 1.35 | $OCH_3$ | $OCH_3$ | H | H | S |
| 1.36 | H | $CH_3$ | H | H | S |
| 1.37 | $CH_3$ | H | H | H | S |
| 1.38 | $CH_3$ | H | $CH_3$ | H | S |
| 1.39 | H | $CH_3$ | H | $CH_3$ | S |
| 1.40 | H | $OCH_3$ | H | H | S |
| 1.41 | $OCH_3$ | H | H | H | S |
| 1.42 | $CH_3$ | H | $CH_3$ | $CH_3$ | S |
| 1.43 | H | $CH_3$ | $CH_3$ | $CH_3$ | S |
| 1.44 | H | H | $CH_3$ | H | S |
| 1.45 | H | H | H | $CH_3$ | S |
| 1.46 | H | H | $OCH_3$ | H | S |
| 1.47 | H | H | H | $OCH_3$ | S |
| 1.48 | H | H | H | H | $N(CH_3)$ |
| 1.49 | $CH_3$ | $CH_3$ | H | H | $N(CH_3)$ |

TABLE 1-continued

| Compound Number | R⁴ | R⁵ | R⁶ | R⁷ | Y |
|---|---|---|---|---|---|
| 1.50 | H | H | H | H | N(C₂H₅) |
| 1.51 | H | H | H | H | NCH₂Ph |
| 1.52 | H | H | H | H | NC(O)CH₃ |
| 1.53 | H | H | H | H | NC(O)OC(CH₃)₃ |
| 1.54 | H | H | H | H | NH |
| 1.55 | H | H | H | H | NC(O)H |
| 1.56 | CH₃ | CH₃ | H | H | NC(O)H |
| 1.57 | CH₃ | CH₃ | H | H | NH |
| 1.58 | CH₃ | CH₃ | H | H | NC(O)CH₃ |
| 1.58 | CH₃ | CH₃ | H | H | NC(O)OC(CH₃)₃ |
| 1.59 | CH₃ | CH₃ | H | H | NCH₂Ph |
| 1.60 | Cl | Cl | H | H | O |
| 1.61 | H | H | H | H | NC(O)OCH₃ |
| 1.62 | H | H | H | H | NCH₂-4-Cl-Ph |
| 1.63 | H | H | H | H | NCH₂-4-CH₃-Ph |
| 1.64 | H | H | H | H | NCH₂-3-Cl-Ph |
| 1.65 | H | H | H | H | NCH₂-3-CF₃-Ph |
| 1.66 | H | H | H | H | NCH₂-3-OCH₃-Ph |
| 1.67 | CH₃ | CH₃ | H | H | NC(O)OCH₃ |
| 1.68 | CH₃ | CH₃ | H | H | NC(O)OC₂H₅ |
| 1.69 | H | H | H | H | NC(O)OC₂H₅ |
| 1.70 | CH₃ | CH₃ | H | H | NC(O)OCH₂CH₂Cl |
| 1.71 | H | H | H | H | NC(O)OCH₂CH₂Cl |
| 1.72 | CH₃ | CH₃ | H | H | NC(O)OC₄H₉-(n) |
| 1.73 | H | H | H | H | NC(O)OC₄H₉-(n) |
| 1.74 | CH₃ | CH₃ | H | H | NC(O)OC₄H₉-(i) |
| 1.75 | H | H | H | H | NC(O)OC₄H₉-(i) |
| 1.76 | H | H | H | H | CH(C₃H₇-(i)) syn or anti |
| 1.77 | H | H | H | H | CH(C₃H₇-(n)) syn or anti |
| 1.78 | H | H | H | H | CH(C₄H₉-(i)) syn or anti |
| 1.79 | H | H | H | H | CH(C₄H₉-(n)) syn or anti |
| 1.80 | H | H | H | H | C(C₂H₄-(c)) |
| 1.81 | H | H | H | H | C(C₄H₈-(c)) |
| 1.82 | H | H | H | H | CHCH(C₂H₅)₂ syn or anti |
| 1.83 | H | H | H | H | CHCH₂(C₃H₅-(c) syn or anti |
| 1.84 | H | H | H | H | CH(C₅H₉-(c) syn or anti |
| 1.85 | H | H | H | H | CHCH₂OAc syn or anti |
| 1.86 | H | H | H | H | CHCHO syn or anti |
| 1.87 | H | H | H | H | CHCH₂OH syn or anti |
| 1.88 | H | H | H | H | CHCH₂—C₆H₅ syn or anti |
| 1.89 | H | H | H | H | C=O |
| 1.90 | H | H | H | H | C(O—C₃H₇-(n))₂ |
| 1.91 | H | H | H | H | C(O—C₂H₅—)₂ |
| 1.92 | H | H | H | H | CH(C₂H₅) syn or anti |
| 1.93 | H | H | H | H | CF₂ |
| 1.94 | H | H | H | H | CH(Cl) syn or anti |

Table 2 provides 111 compounds of formula (D) wherein Y, R⁴, R⁵, R⁶ and R⁷ are as defined in Table 2.

TABLE 2

| Cmpd. No. | R⁴ | R⁵ | R⁶ | R⁷ | Y |
|---|---|---|---|---|---|
| 2.01 | CH₃ | CH₃ | H | H | O |
| 2.02 | CH₃ | H | H | H | O |
| 2.03 | H | CH₃ | H | H | O |
| 2.04 | CH₃ | CH₃ | C(O)CH₃ | H | O |
| 2.05 | CH₃ | CH₃ | H | C(O)CH₃ | O |
| 2.06 | CH₃ | C(O)CH₃ | H | H | O |
| 2.07 | C(O)CH₃ | CH₃ | H | H | O |
| 2.08 | C(O)OCH₃ | H | H | H | O |
| 2.09 | H | C(O)OCH₃ | H | H | O |
| 2.10 | H | H | H | H | O |
| 2.11 | CF₃ | CF₃ | H | H | O |
| 2.12 | OCH₃ | OCH₃ | H | H | O |
| 2.13 | H | H | CH₃ | CH₃ | O |
| 2.14 | C₂H₅ | C₂H₅ | H | H | O |
| 2.15 | CH₃ | H | CH₃ | H | O |
| 2.16 | H | H | H | H | CH₂ |
| 2.17 | CH₃ | H | CH₃ | H | CH₂ |
| 2.18 | H | CH₃ | H | CH₃ | CH₂ |
| 2.19 | CH₃ | CH₃ | CH₃ | CH₃ | CH₂ |

TABLE 2-continued

| Cmpd. No. | R⁴ | R⁵ | R⁶ | R⁷ | Y |
|---|---|---|---|---|---|
| 2.20 | CH₃ | CH₃ | CH₃ | CH₃ | CH(CH₃) syn or anti |
| 2.21 | H | H | H | H | CH(CH₃) syn or anti |
| 2.22 | H | H | H | H | CH(C₂H₅) syn or anti |
| 2.23 | H | H | H | H | CH₂CH₂ |
| 2.24 | CH₃ | CH₃ | H | H | CH₂CH₂ |
| 2.25 | H | H | CH₃ | CH₃ | CH₂CH₂ |
| 2.26 | H | H | OCH₃ | H | CH₂CH₂ |
| 2.27 | H | H | H | OCH₃ | CH₂CH₂ |
| 2.28 | H | H | H | H | CH₂CH₂CH₂ |
| 2.29 | H | H | CH₃ | CH₃ | C(CH₃)₂ |
| 2.30 | CH₃ | CH₃ | CH₃ | CH₃ | C(CH₃)₂ |
| 2.31 | CH₃ | H | CH₃ | H | C(CH₃)₂ |
| 2.32 | H | CH₃ | H | CH₃ | C(CH₃)₂ |
| 2.33 | CH₃ | CH₃ | CH₃ | CH₃ | C(CH₃)(C₂H₅) |
| 2.34 | H | H | H | H | C(CH₃)₂ |
| 2.35 | CH₃ | CH₃ | H | H | C(CH₃)₂ |
| 2.36 | H | H | H | H | CH(OCH₃) syn or anti |
| 2.37 | H | H | H | H | S |
| 2.38 | CH₃ | CH₃ | H | H | S |
| 2.39 | H | H | CH₃ | CH₃ | S |
| 2.40 | OCH₃ | OCH₃ | H | H | S |
| 2.41 | H | CH₃ | H | H | S |
| 2.42 | CH₃ | H | H | H | S |
| 2.43 | CH₃ | H | CH₃ | H | S |
| 2.44 | H | CH₃ | H | CH₃ | S |
| 2.45 | H | OCH₃ | H | H | S |
| 2.46 | OCH₃ | H | H | H | S |
| 2.47 | CH₃ | H | CH₃ | CH₃ | S |
| 2.48 | H | CH₃ | CH₃ | CH₃ | S |
| 2.49 | H | H | CH₃ | H | S |
| 2.50 | H | H | H | CH₃ | S |
| 2.51 | H | H | OCH₃ | H | S |
| 2.52 | H | H | H | OCH₃ | S |
| 2.53 | H | H | H | H | N(CH₃) |
| 2.54 | CH₃ | CH₃ | H | H | N(CH₃) |
| 2.55 | H | H | H | H | N(C₂H₅) |
| 2.56 | H | H | H | H | NCH₂Ph |
| 2.57 | H | H | H | H | NC(O)CH₃ |
| 2.58 | H | H | H | H | NC(O)OC(CH₃)₃ |
| 2.59 | H | H | H | H | NH |
| 2.60 | Cl | Cl | H | H | O |
| 2.61 | H | H | H | H | NC(O)H |
| 2.62 | CH₃ | CH₃ | H | H | NC(O)H |
| 2.63 | CH₃ | CH₃ | H | H | NH |
| 2.64 | CH₃ | CH₃ | H | H | NC(O)CH₃ |
| 2.65 | CH₃ | CH₃ | H | H | NC(O)OC(CH₃)₃ |
| 2.66 | CH₃ | CH₃ | H | H | NCH₂Ph |
| 2.67 | H | H | H | H | NC(O)OCH₃ |
| 2.68 | H | H | H | H | NCH₂-4-Cl-Ph |
| 2.69 | H | H | H | H | NCH₂-4-CH₃-Ph |
| 2.70 | H | H | H | H | NCH₂-3-Cl-Ph |
| 2.71 | H | H | H | H | NCH₂-3-CF₃-Ph |
| 2.72 | H | H | H | H | NCH₂-3-OCH₃-Ph |
| 2.73 | CH₃ | CH₃ | H | H | NC(O)OCH₃ |
| 2.74 | CH₃ | CH₃ | H | H | NC(O)OC₂H₅ |
| 2.75 | H | H | H | H | NC(O)OC₂H₅ |
| 2.76 | CH₃ | CH₃ | H | H | NC(O)OCH₂CH₂Cl |
| 2.77 | H | H | H | H | NC(O)OCH₂CH₂Cl |
| 2.78 | CH₃ | CH₃ | H | H | NC(O)OC₄H₉-(n) |
| 2.79 | H | H | H | H | NC(O)OC₄H₉-(n) |
| 2.80 | CH₃ | CH₃ | H | H | NC(O)OC₄H₉-(i) |
| 2.81 | H | H | H | H | NC(O)OC₄H₉-(i) |
| 2.82 | H | H | H | H | CH(C₃H₇-(i)) syn or anti |
| 2.83 | H | H | H | H | CH(C₃H₇-(n)) syn or anti |
| 2.84 | H | H | H | H | CH(C₄H₉-(i)) syn or anti |
| 2.85 | H | H | H | H | CH(C₄H₉-(n)) syn or anti |
| 2.86 | H | H | H | H | C(C₂H₄-(c)) |
| 2.87 | H | H | H | H | C(C₄H₈-(c)) |
| 2.88 | H | H | H | H | CHCH(C₂H₅)₂ syn or anti |
| 2.89 | H | H | H | H | CHCH₂(C₃H₅-(c)) syn or anti |
| 2.90 | H | H | H | H | CH(C₅H₉-(c)) syn or anti |
| 2.91 | H | H | H | H | CHCH₂OAc syn or anti |
| 2.92 | H | H | H | H | CHCHO syn or anti |
| 2.93 | H | H | H | H | CHCH₂OH syn or anti |
| 2.94 | H | H | H | H | CHCH₂—C₆H₅ syn or anti |
| 2.95 | H | H | H | H | C=O |
| 2.96 | H | H | H | H | C(O—C₃H₇-(n))₂ |

TABLE 2-continued

| Cmpd. No. | R⁴ | R⁵ | R⁶ | R⁷ | Y |
|---|---|---|---|---|---|
| 2.97 | H | H | H | H | C(O—C$_2$H$_5$)$_2$ |
| 2.98 | H | H | H | H | C(O—C$_3$H$_7$-(i))$_2$ |
| 2.99 | H | H | H | H | C(O—CH$_3$)$_2$ |
| 2.100 | H | H | H | H | C(OH)CH$_3$ syn or anti |
| 2.101 | H | H | H | H | C(OH)C$_2$H$_5$ syn or anti |
| 2.102 | H | H | H | H | 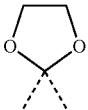 |
| 2.103 | H | H | H | H | CF$_2$ |
| 2.104 | H | H | H | H | CH(F) syn or anti |
| 2.105 | H | H | H | H | C(CH$_3$)(C$_2$H$_5$) syn or anti |
| 2.106 | H | H | H | H | C=C(CH$_3$)$_2$ |
| 2.107 | H | H | H | H | C=C(C$_2$H$_5$)$_2$ |
| 2.108 | H | H | H | H | C=cC$_5$H$_8$ |
| 2.109 | H | H | H | H | C=CH(CH$_3$) |
| 2.110 | H | H | H | H | C=CH(C$_2$H$_5$) |
| 2.111 | H | H | H | H | C=cC$_3$H$_4$ |

Table Z represents Table 3 [when Z is 3], Table 4 [when Z is 4], Table 5 [when Z is 5], Table 6 [when Z is 6], Table 7 [when Z is 7], Table 8 [when Z is 8], Table 9 [when Z is 9], Table 10 [when Z is 10], Table 11 [when Z is 11], Table 12 [when Z is 12], Table 13 [when Z is 13], Table 14 [when Z is 14], Table 15 [when Z is 15], Table 16 [when Z is 16], Table 17 [when Z is 17], Table 18 [when Z is 18], Table 19 [when Z is 19], Table 20 [when Z is 20], Table 21 [when Z is 21], Table 22 [when Z is 22], Table 23 [when Z is 23], Table 24 [when Z is 24], Table 25 [when Z is 25], Table 26 [when Z is 26], Table 27 [when Z is 27], Table 28 [when Z is 28] and represents Table 29 [when Z is 29]. X is either a single bond (—) or a double bond (=).

TABLE Z

| Cpd. No. | R¹ | R⁴ | R⁵ | R⁶ | R⁷ | X | Y |
|---|---|---|---|---|---|---|---|
| Z.001 | H | CH$_3$ | CH$_3$ | H | H | = | O |
| Z.002 | CH$_2$C≡CH | CH$_3$ | CH$_3$ | H | H | = | O |
| Z.003 | CH=C=CH$_2$ | CH$_3$ | CH$_3$ | H | H | = | O |
| Z.004 | C(O)CH$_3$ | CH$_3$ | CH$_3$ | H | H | = | O |
| Z.005 | H | CH$_3$ | H | H | H | = | O |
| Z.006 | H | H | CH$_3$ | H | H | = | O |
| Z.007 | H | CH$_3$ | CH$_3$ | C(O)CH$_3$ | H | = | O |
| Z.008 | H | CH$_3$ | CH$_3$ | H | C(O)CH$_3$ | = | O |
| Z.009 | H | CH$_3$ | C(O)CH$_3$ | H | H | = | O |
| Z.010 | H | C(O)CH$_3$ | CH$_3$ | H | H | = | O |
| Z.011 | H | COOCH$_3$ | H | H | H | = | O |
| Z.012 | H | H | COOCH$_3$ | H | H | = | O |
| Z.013 | H | H | H | H | H | = | O |
| Z.014 | CH$_2$C≡CH | H | H | H | H | = | O |
| Z.015 | CH=C=CH$_2$ | H | H | H | H | = | O |
| Z.016 | COCH$_3$ | H | H | H | H | = | O |
| Z.017 | H | CF$_3$ | CF$_3$ | H | H | = | O |
| Z.018 | H | OCH$_3$ | OCH$_3$ | H | H | = | O |
| Z.019 | H | H | H | CH$_3$ | CH$_3$ | = | O |
| Z.020 | H | C$_2$H$_5$ | C$_2$H$_5$ | H | H | = | O |
| Z.021 | H | CH3 | H | CH$_3$ | H | = | O |
| Z.022 | H | H | CH3 | H | CH$_3$ | = | O |
| Z.023 | H | CH$_3$ | CH$_3$ | H | H | — | O |
| Z.024 | CH$_2$C≡CH | CH$_3$ | CH$_3$ | H | H | — | O |
| Z.025 | CH=C=CH$_2$ | CH$_3$ | CH$_3$ | H | H | — | O |
| Z.026 | COCH$_3$ | CH$_3$ | CH$_3$ | H | H | — | O |
| Z.027 | H | CH$_3$ | H | H | H | — | O |
| Z.028 | H | H | CH$_3$ | H | H | — | O |
| Z.029 | H | CH$_3$ | CH$_3$ | C(O)CH$_3$ | H | — | O |
| Z.030 | H | CH$_3$ | CH$_3$ | H | C(O)CH$_3$ | — | O |
| Z.031 | H | CH$_3$ | C(O)CH3 | H | H | — | O |
| Z.032 | H | C(O)CH$_3$ | CH$_3$ | H | H | — | O |
| Z.033 | H | COOCH$_3$ | H | H | H | — | O |
| Z.034 | H | H | COOCH$_3$ | H | H | — | O |
| Z.035 | H | H | H | H | H | — | O |
| Z.036 | CH$_2$C≡CH | H | H | H | H | — | O |
| Z.037 | CH=C=CH$_2$ | H | H | H | H | — | O |
| Z.038 | COCH$_3$ | H | H | H | H | — | O |

TABLE Z-continued

| Cpd. No. | $R^1$ | $R^4$ | $R^5$ | $R^6$ | $R^7$ | X | Y |
|---|---|---|---|---|---|---|---|
| Z.039 | H | H | H | H | H | — | O |
| Z.040 | H | $CF_3$ | $CF_3$ | H | H | — | O |
| Z.041 | H | $OCH_3$ | $OCH_3$ | H | H | — | O |
| Z.042 | H | H | H | $CH_3$ | $CH_3$ | — | O |
| Z.043 | $CH_2C\equiv CH$ | H | H | $CH_3$ | $CH_3$ | — | O |
| Z.044 | $CH=C=CH_2$ | H | H | $CH_3$ | $CH_3$ | — | O |
| Z.045 | $COCH_3$ | H | H | $CH_3$ | $CH_3$ | — | O |
| Z.046 | H | $C_2H_5$ | $C_2H_5$ | H | H | — | O |
| Z.047 | H | $CH_3$ | H | $CH_3$ | H | — | O |
| Z.048 | H | H | H | H | H | — | $CH_2$ |
| Z.049 | $CH_2C\equiv CH$ | H | H | H | H | — | $CH_2$ |
| Z.050 | $CH=C=CH_2$ | H | H | H | H | — | $CH_2$ |
| Z.051 | $COCH_3$ | H | H | H | H | — | $CH_2$ |
| Z.052 | H | H | H | H | H | = | $CH_2$ |
| Z.053 | $CH_2C\equiv CH$ | H | H | H | H | = | $CH_2$ |
| Z.054 | $CH=C=CH_2$ | H | H | H | H | = | $CH_2$ |
| Z.055 | $COCH_3$ | H | H | H | H | = | $CH_2$ |
| Z.056 | H | $CH_3$ | H | $CH_3$ | H | — | $CH_2$ |
| Z.057 | H | $CH_3$ | H | $CH_3$ | H | = | $CH_2$ |
| Z.058 | H | H | $CH_3$ | H | $CH_3$ | — | $CH_2$ |
| Z.059 | H | H | $CH_3$ | H | $CH_3$ | = | $CH_2$ |
| Z.060 | H | $CH_3$ | $CH_3$ | $CH_3$ | $CH_3$ | = | $CH_2$ |
| Z.061 | H | $CH_3$ | $CH_3$ | $CH_3$ | $CH_3$ | — | $CH_2$ |
| Z.062 | $CH_2C\equiv CH$ | $CH_3$ | $CH_3$ | $CH_3$ | $CH_3$ | — | $CH_2$ |
| Z.063 | $CH=C=CH_2$ | $CH_3$ | $CH_3$ | $CH_3$ | $CH_3$ | — | $CH_2$ |
| Z.064 | $COCH_3$ | $CH_3$ | $CH_3$ | $CH_3$ | $CH_3$ | — | $CH_2$ |
| Z.065 | H | $CH_3$ | $CH_3$ | $CH_3$ | $CH_3$ | = | $CH(CH_3)$ syn or anti |
| Z.066 | H | $CH_3$ | $CH_3$ | $CH_3$ | $CH_3$ | — | $CH(CH_3)$ syn or anti |
| Z.067 | $CH_2C\equiv CH$ | $CH_3$ | $CH_3$ | $CH_3$ | $CH_3$ | — | $CH(CH_3)$ syn or anti |
| Z.068 | $CH=C=CH_2$ | $CH_3$ | $CH_3$ | $CH_3$ | $CH_3$ | — | $CH(CH_3)$ syn or anti |
| Z.069 | $COCH_3$ | $CH_3$ | $CH_3$ | $CH_3$ | $CH_3$ | — | $CH(CH_3)$ syn or anti |
| Z.070 | H | H | H | H | H | = | $CH(CH_3)$ syn or anti |
| Z.071 | H | H | H | H | H | — | $CH(CH_3)$ syn or anti |
| Z.072 | $CH_2C\equiv CH$ | H | H | H | H | — | $CH(CH_3)$ syn or anti |
| Z.073 | $CH=C=CH_2$ | H | H | H | H | — | $CH(CH_3)$ syn or anti |
| Z.074 | $COCH_3$ | H | H | H | H | — | $CH(CH_3)$ syn or anti |
| Z.075 | H | H | H | H | H | — | $CH(C_2H_5)$ syn or anti |
| Z.076 | H | H | H | H | H | — | $CH_2CH_2$ |
| Z.077 | $CH_2C\equiv CH$ | H | H | H | H | — | $CH_2CH_2$ |
| Z.078 | $CH=C=CH_2$ | H | H | H | H | — | $CH_2CH_2$ |
| Z.079 | $COCH_3$ | H | H | H | H | — | $CH_2CH_2$ |
| Z.080 | H | $CH_3$ | $CH_3$ | H | H | = | $CH_2CH_2$ |
| Z.081 | H | $CH_3$ | $CH_3$ | H | H | — | $CH_2CH_2$ |
| Z.082 | H | H | H | $CH_3$ | $CH_3$ | = | $CH_2CH_2$ |
| Z.083 | H | H | H | $CH_3$ | $CH_3$ | — | $CH_2CH_2$ |
| Z.084 | H | H | H | $OCH_3$ | H | — | $CH_2CH_2$ |
| Z.085 | H | H | H | H | $OCH_3$ | — | $CH_2CH_2$ |
| Z.086 | H | H | H | H | H | — | $CH_2CH_2CH_2$ |
| Z.087 | H | H | H | H | H | = | $CH_2CH_2CH_2$ |
| Z.088 | H | H | H | $CH_3$ | $CH_3$ | = | $C(CH_3)_2$ |
| Z.089 | H | H | H | $CH_3$ | $CH_3$ | — | $C(CH_3)_2$ |
| Z.090 | $CH_2C\equiv CH$ | H | H | $CH_3$ | $CH_3$ | — | $C(CH_3)_2$ |
| Z.091 | $CH=C=CH_2$ | H | H | $CH_3$ | $CH_3$ | — | $C(CH_3)_2$ |
| Z.092 | $COCH_3$ | H | H | $CH_3$ | $CH_3$ | — | $C(CH_3)_2$ |
| Z.093 | H | $CH_3$ | $CH_3$ | $CH_3$ | $CH_3$ | = | $C(CH_3)_2$ |
| Z.094 | H | $CH_3$ | $CH_3$ | $CH_3$ | $CH_3$ | — | $C(CH_3)_2$ |
| Z.095 | H | $CH_3$ | H | $CH_3$ | H | — | $C(CH_3)_2$ |
| Z.096 | H | H | $CH_3$ | H | $CH_3$ | — | $C(CH_3)_2$ |
| Z.097 | H | $CH_3$ | H | $CH_3$ | H | = | $C(CH_3)_2$ |
| Z.098 | H | H | $CH_3$ | H | $CH_3$ | = | $C(CH_3)_2$ |
| Z.099 | H | $CH_3$ | $CH_3$ | $CH_3$ | $CH_3$ | — | $C(CH_3)(C_2H_5)$ |
| Z.100 | H | H | H | H | H | — | $C(CH_3)_2$ |
| Z.101 | $CH_2C\equiv CH$ | H | H | H | H | — | $C(CH_3)_2$ |
| Z.102 | H | H | H | H | H | = | $C(CH_3)_2$ |
| Z.103 | H | $CH_3$ | $CH_3$ | H | H | — | $C(CH_3)_2$ |
| Z.104 | H | $CH_3$ | $CH_3$ | H | H | — | $C(CH_3)_2$ |
| Z.105 | H | H | H | H | H | = | $C(OCH_3)_2$ |
| Z.106 | H | H | H | H | H | — | $CH(OCH_3)$ syn or anti |
| Z.107 | H | H | H | H | H | = | S |
| Z.108 | $CH_2C\equiv CH$ | H | H | H | H | = | S |
| Z.109 | $CH=C=CH_2$ | H | H | H | H | = | S |

TABLE Z-continued

| Cpd. No. | R$^1$ | R$^4$ | R$^5$ | R$^6$ | R$^7$ | X | Y |
|---|---|---|---|---|---|---|---|
| Z.110 | COCH$_3$ | H | H | H | H | = | S |
| Z.111 | H | H | H | H | H | — | S |
| Z.112 | CH$_2$C≡CH | H | H | H | H | — | S |
| Z.113 | CH=C=CH$_2$ | H | H | H | H | — | S |
| Z.114 | COCH$_3$ | H | H | H | H | — | S |
| Z.115 | H | CH$_3$ | CH$_3$ | H | H | = | S |
| Z.116 | H | CH$_3$ | CH$_3$ | H | H | — | S |
| Z.117 | CH$_2$C≡CH | CH$_3$ | CH$_3$ | H | H | — | S |
| Z.118 | CH=C=CH$_2$ | CH$_3$ | CH$_3$ | H | H | — | S |
| Z.119 | COCH$_3$ | CH$_3$ | CH$_3$ | H | H | — | S |
| Z.120 | H | H | H | CH$_3$ | CH$_3$ | = | S |
| Z.121 | H | H | H | CH$_3$ | CH$_3$ | — | S |
| Z.122 | CH$_2$C≡CH | H | H | CH$_3$ | CH$_3$ | — | S |
| Z.123 | CH=C=CH$_2$ | H | H | CH$_3$ | CH$_3$ | — | S |
| Z.124 | COCH$_3$ | H | H | CH$_3$ | CH$_3$ | — | S |
| Z.125 | H | OCH$_3$ | OCH$_3$ | H | H | = | S |
| Z.126 | H | OCH$_3$ | OCH$_3$ | H | H | — | S |
| Z.127 | H | H | CH$_3$ | H | H | = | S |
| Z.128 | H | H | CH$_3$ | H | H | — | S |
| Z.129 | H | CH$_3$ | H | H | H | = | S |
| Z.130 | H | CH$_3$ | H | H | H | — | S |
| Z.131 | H | CH$_3$ | H | CH$_3$ | H | = | S |
| Z.132 | H | CH$_3$ | H | CH$_3$ | H | — | S |
| Z.133 | H | H | CH$_3$ | H | CH$_3$ | = | S |
| Z.134 | H | H | CH$_3$ | H | CH$_3$ | — | S |
| Z.135 | H | H | OCH$_3$ | H | H | = | S |
| Z.136 | H | H | OCH$_3$ | H | H | — | S |
| Z.137 | H | OCH$_3$ | H | H | H | = | S |
| Z.138 | H | OCH$_3$ | H | H | H | — | S |
| Z.139 | H | CH$_3$ | H | CH$_3$ | CH$_3$ | = | S |
| Z.140 | H | CH$_3$ | H | CH$_3$ | CH$_3$ | — | S |
| Z.141 | H | H | CH$_3$ | CH$_3$ | CH$_3$ | = | S |
| Z.142 | H | H | CH$_3$ | CH$_3$ | CH$_3$ | — | S |
| Z.143 | H | H | H | CH$_3$ | H | = | S |
| Z.144 | H | H | H | CH$_3$ | H | — | S |
| Z.145 | H | H | H | H | CH$_3$ | = | S |
| Z.146 | H | H | H | H | CH$_3$ | — | S |
| Z.147 | H | H | H | OCH$_3$ | H | = | S |
| Z.148 | H | H | H | OCH$_3$ | H | — | S |
| Z.149 | H | H | H | H | OCH$_3$ | = | S |
| Z.150 | H | H | H | H | OCH$_3$ | — | S |
| Z.151 | H | H | H | H | H | = | N(CH$_3$) |
| Z.152 | H | H | H | H | H | — | N(CH$_3$) |
| Z.153 | CH$_2$C≡CH | H | H | H | H | — | N(CH$_3$) |
| Z.154 | CH=C=CH$_2$ | H | H | H | H | — | N(CH$_3$) |
| Z.155 | COCH$_3$ | H | H | H | H | — | N(CH$_3$) |
| Z.156 | H | CH$_3$ | CH$_3$ | H | H | = | N(CH$_3$) |
| Z.157 | H | CH$_3$ | CH$_3$ | H | H | — | N(CH$_3$) |
| Z.158 | CH$_2$C≡CH | CH$_3$ | CH$_3$ | H | H | — | N(CH$_3$) |
| Z.159 | CH=C=CH$_2$ | CH$_3$ | CH$_3$ | H | H | — | N(CH$_3$) |
| Z.160 | COCH$_3$ | CH$_3$ | CH$_3$ | H | H | — | N(CH$_3$) |
| Z.161 | H | H | H | H | H | = | N(C$_2$H$_5$) |
| Z.162 | H | H | H | H | H | — | N(C$_2$H$_5$) |
| Z.163 | H | H | H | H | H | = | NCH$_2$Ph |
| Z.164 | H | H | H | H | H | — | NCH$_2$Ph |
| Z.165 | H | H | H | H | H | = | NC(O)CH$_3$ |
| Z.166 | H | H | H | H | H | — | NC(O)CH$_3$ |
| Z.167 | H | H | H | H | H | = | NC(O)OC(CH$_3$)$_3$ |
| Z.168 | H | H | H | H | H | — | NC(O)OC(CH$_3$)$_3$ |
| Z.169 | H | H | H | H | H | = | NH |
| Z.170 | H | H | H | H | H | — | NH |
| Z.171 | H | H | H | H | H | = | NC(O)H |
| Z.172 | H | H | H | H | H | — | NC(O)H |
| Z.173 | H | CH$_3$ | CH$_3$ | H | H | = | NCH$_2$Ph |
| Z.174 | H | CH$_3$ | CH$_3$ | H | H | — | NCH$_2$Ph |
| Z.175 | H | CH$_3$ | CH$_3$ | H | H | = | NC(O)CH$_3$ |
| Z.176 | H | CH$_3$ | CH$_3$ | H | H | — | NC(O)CH$_3$ |
| Z.177 | H | CH$_3$ | CH$_3$ | H | H | = | NC(O)OC(CH$_3$)$_3$ |
| Z.178 | H | CH$_3$ | CH$_3$ | H | H | — | NC(O)OC(CH$_3$)$_3$ |
| Z.179 | H | CH$_3$ | CH$_3$ | H | H | = | NH |
| Z.180 | H | CH$_3$ | CH$_3$ | H | H | — | NH |

TABLE Z-continued

| Cpd. No. | $R^1$ | $R^4$ | $R^5$ | $R^6$ | $R^7$ | X | Y |
|---|---|---|---|---|---|---|---|
| Z.181 | H | $CH_3$ | $CH_3$ | H | H | = | NC(O)H |
| Z.182 | H | $CH_3$ | $CH_3$ | H | H | — | NC(O)H |
| Z.183 | H | H | H | H | H | — | $NC(O)OCH_3$ |
| Z.184 | H | H | H | H | H | — | $NCH_2$-4-Cl-Ph |
| Z.185 | H | H | H | H | H | — | $NCH_2$-4-$CH_3$-Ph |
| Z.186 | H | H | H | H | H | — | $NCH_2$-3-Cl-Ph |
| Z.187 | H | H | H | H | H | — | $NCH_3$-3-$CF_3$-Ph |
| Z.188 | H | H | H | H | H | — | $NCH_2$-3-$OCH_3$-Ph |
| Z.189 | H | $CH_3$ | $CH_3$ | H | H | — | $NC(O)OCH_3$ |
| Z.190 | H | $CH_3$ | $CH_3$ | H | H | — | $NC(O)OC_2H_5$ |
| Z.191 | H | H | H | H | H | — | $NC(O)OC_2H_5$ |
| Z.192 | H | $CH_3$ | $CH_3$ | H | H | — | $NC(O)OCH_2CH_2Cl$ |
| Z.193 | H | H | H | H | H | — | $NC(O)OCH_2CH_2Cl$ |
| Z.194 | H | $CH_3$ | $CH_3$ | H | H | — | $NC(O)OC_4H_9$-(n) |
| Z.195 | H | H | H | H | H | — | $NC(O)OC_4H_9$-(n) |
| Z.196 | H | $CH_3$ | $CH_3$ | H | H | — | $NC(O)OC_4H_9$-(i) |
| Z.197 | H | H | H | H | H | — | $NC(O)OC_4H_9$-(i) |
| Z.198 | H | $CH_3$ | $CH_3$ | H | H | — | $NC(O)OC_3H_7$-(n) |
| Z.199 | H | H | H | H | H | — | $NC(O)OC_3H_7$-(n) |
| Z.200 | H | $CH_3$ | $CH_3$ | H | H | — | $NC(O)OC_3H_7$-(i) |
| Z.201 | H | H | H | H | H | — | $NC(O)OC_3H_7$-(i) |
| Z.202 | H | H | H | H | H | — | $CH(C_7H_7$-(i)) syn or anti |
| Z.203 | $CH_2C{\equiv}CH$ | H | H | H | H | — | $CH(C_3H_7$-(i)) syn or anti |
| Z.204 | $CH{=}C{=}CH_2$ | H | H | H | H | — | $CH(C_3H_7$-(i)) syn or anti |
| Z.205 | $COCH_3$ | H | H | H | H | — | $CH(C_3H_7$-(i)) syn or anti |
| Z.206 | H | H | H | H | H | = | $CH(C_3H_7$-(i)) syn or anti |
| Z.207 | H | H | H | H | H | — | $CH(C_3H_7$-(n)) syn or anti |
| Z.208 | H | H | H | H | H | — | $CH(C_4H_9$-(i)) syn or anti |
| Z.209 | H | H | H | H | H | — | $CH(C_4H_9$-(n)) syn or anti |
| Z.210 | H | H | H | H | H | — | $C(C_2H_4$-(c)) |
| Z.211 | H | H | H | H | H | — | $C(C_4H_8$-(c)) |
| Z.212 | H | H | H | H | H | — | $CHCH(C_2H_5)_2$ syn or anti |
| Z.213 | H | H | H | H | H | — | $CHCH_2(C_3H_5$-(c)) syn or anti |
| Z.214 | H | H | H | H | H | — | $CH(C_5H_9$-(c)) syn or anti |
| Z.215 | H | H | H | H | H | — | $CHCH_2OAc$ syn or anti |
| Z.216 | H | H | H | H | H | — | $CHCHO$ syn or anti |
| Z.217 | H | H | H | H | H | — | $CHCH_2OH$ syn or anti |
| Z.218 | H | H | H | H | H | — | $CHCH_2{-}C_6H_5$ syn or anti |
| Z.219 | H | H | H | H | H | — | C=O |
| Z.220 | H | H | H | H | H | — | $C(O{-}C_3H_7$-(n))$_2$ |
| Z.221 | H | H | H | H | H | — | $C(O{-}C_2H_5)_2$ |
| Z.222 | H | H | H | H | H | — | $C(OH)CH_3$ syn or anti |
| Z.223 | H | H | H | H | H | — | $C(OH)C_2H_5$ syn or anti |
| Z.224 | H | H | H | H | H | — |  |
| Z.225 | H | H | H | H | H | — | $CHCH(Ph)_2$ syn or anti |
| Z.226 | H | H | H | H | H | — | $CF_2$ |
| Z.227 | H | H | H | H | H | — | CH(F) syn or anti |
| Z.228 | H | H | H | H | H | — | $C(C_2H_5)(CH_3)$ syn or anti |
| Z.229 | H | H | H | H | H | — | $CH(sec{-}C_4H_9)$ syn or anti |
| Z.230 | H | H | H | H | H | — | $C{=}C(CH_3)_2$ |
| Z.231 | H | H | H | H | H | — | $C{=}C(C_2H_5)_2$ |
| Z.232 | H | H | H | H | H | — | $C{=}cC_5H_8$ |
| Z.233 | H | H | H | H | H | — | $C{=}CH(CH_3)$ |
| Z.234 | H | H | H | H | H | — | $C{=}CH(C_2H_5)$ |
| Z.235 | H | H | H | H | H | — | $C{=}cC_3H_4$ |

Table 3 provides 235 compounds of formula (I) where Het is

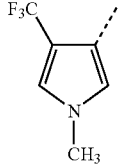

$R^2$ and $R^3$ are both hydrogen; and X, Y, $R^1$, $R^4$, $R^5$, $R^6$ and $R^7$ are as defined in Table 3.

Table 4 provides 235 compounds of formula (I) where Het is

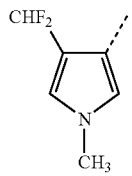

$R^2$ and $R^3$ are both hydrogen; and X, Y, $R^1$, $R^4$, $R^5$, $R^6$ and $R^7$ are as defined in Table 4.

Table 5 provides 235 compounds of formula (I) where Het is

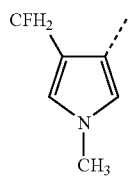

$R^2$ and $R^3$ are both hydrogen; and X, Y, $R^1$, $R^4$, $R^5$, $R^6$ and $R^7$ are as defined in Table 5.

Table 6 provides 235 compounds of formula (I) where Het is

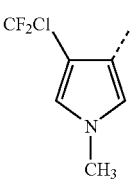

$R^2$ and $R^3$ are both hydrogen; and X, Y, $R^1$, $R^4$, $R^5$, $R^6$ and $R^7$ are as defined in Table 6.

Table 7 provides 235 compounds of formula (I) where Het is

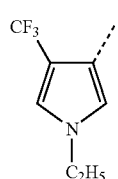

$R^2$ and $R^3$ are both hydrogen; and X, Y, $R^1$, $R^4$, $R^5$, $R^6$ and $R^7$ are as defined in Table 7.

Table 8 provides 235 compounds of formula (I) where Het is

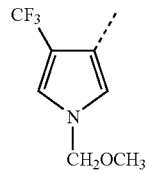

$R^2$ and $R^3$ are both hydrogen; and X, Y, $R^1$, $R^4$, $R^5$, $R^6$ and $R^7$ are as defined in Table 8.

Table 9 provides 235 compounds of formula (I) where Het is

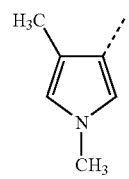

$R^2$ and $R^3$ are both hydrogen; and X, Y, $R^1$, $R^4$, $R^5$, $R^6$ and $R^7$ are as defined in Table 9.

Table 10 provides 235 compounds of formula (I) where Het is

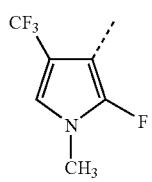

$R^2$ and $R^3$ are both hydrogen; and X, Y, $R^1$, $R^4$, $R^5$, $R^6$ and $R^7$ are as defined in Table 10.

Table 11 provides 235 compounds of formula (I) where Het is

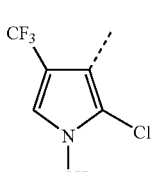

Table 12 provides 235 compounds of formula (I) where Het is

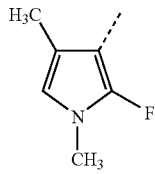

$R^2$ and $R^3$ are both hydrogen; and X, Y, $R^1$, $R^4$, $R^5$, $R^6$ and $R^7$ are as defined in Table 12.

Table 13 provides 235 compounds of formula (I) where Het is

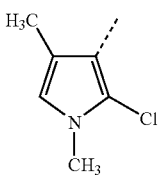

$R^2$ and $R^3$ are both hydrogen; and X, Y, $R^1$, $R^4$, $R^5$, $R^6$ and $R^7$ are as defined in Table 13.

Table 14 provides 235 compounds of formula (I) where Het is

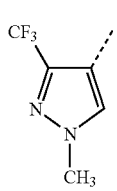

$R^2$ and $R^3$ are both hydrogen; and X, Y, $R^1$, $R^4$, $R^5$, $R^6$ and $R^7$ are as defined in Table 14.

Table 15 provides 235 compounds of formula (I) where Het is

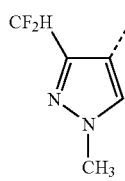

$R^2$ and $R^3$ are both hydrogen; and X, Y, $R^1$, $R^4$, $R^5$, $R^6$ and $R^7$ are as defined in Table 15.

Table 16 provides 235 compounds of formula (I) where Het is

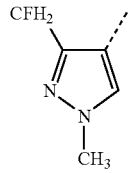

$R^2$ and $R^3$ are both hydrogen; and X, Y, $R^1$, $R^4$, $R^5$, $R^6$ and $R^7$ are as defined in Table 16.

Table 17 provides 235 compounds of formula (I) where Het is

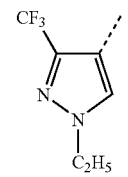

$R^2$ and $R^3$ are both hydrogen; and X, Y, $R^1$, $R^4$, $R^5$, $R^6$ and $R^7$ are as defined in Table 17.

Table 18 provides 235 compounds of formula (I) where Het is

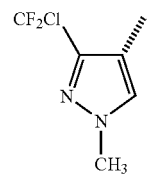

$R^2$ and $R^3$ are both hydrogen; and X, Y, $R^1$, $R^4$, $R^5$, $R^6$ and $R^7$ are as defined in Table 18.

Table 19 provides 235 compounds of formula (I) where Het is

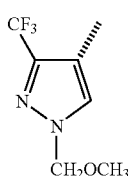

$R^2$ and $R^3$ are both hydrogen; and X, Y, $R^1$, $R^4$, $R^5$, $R^6$ and $R^7$ are as defined in Table 19.

Table 20 provides 235 compounds of formula (I) where Het is

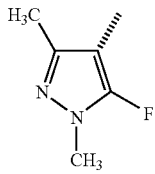

$R^2$ and $R^3$ are both hydrogen; and X, Y, $R^1$, $R^4$, $R^5$, $R^6$ and $R^7$ are as defined in Table 20.

Table 21 provides 235 compounds of formula (I) where Het is

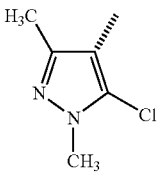

$R^2$ and $R^3$ are both hydrogen; and X, Y, $R^1$, $R^4$, $R^5$, $R^6$ and $R^7$ are as defined in Table 21.

Table 22 provides 235 compounds of formula (I) where Het is

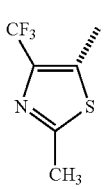

$R^2$ and $R^3$ are both hydrogen; and X, Y, $R^1$, $R^4$, $R^5$, $R^6$ and $R^7$ are as defined in Table 22.

Table 23 provides 235 compounds of formula (I) where Het is

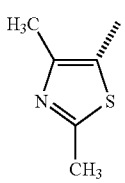

$R^2$ and $R^3$ are both hydrogen; and X, Y, $R^1$, $R^4$, $R^5$, $R^6$ and $R^7$ are as defined in Table 23.

Table 24 provides 235 compounds of formula (I) where Het is

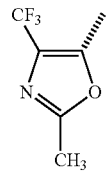

$R^2$ and $R^3$ are both hydrogen; and X, Y, $R^1$, $R^4$, $R^5$, $R^6$ and $R^7$ are as defined in Table 24.

Table 25 provides 235 compounds of formula (I) where Het is

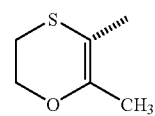

$R^2$ and $R^3$ are both hydrogen; and X, Y, $R^1$, $R^4$, $R^5$, $R^6$ and $R^7$ are as defined in Table 25.

Table 26 provides 235 compounds of formula (I) where Het is

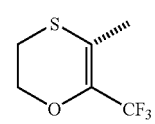

$R^2$ and $R^3$ are both hydrogen; and X, Y, $R^1$, $R^4$, $R^5$, $R^6$ and $R^7$ are as defined in Table 26.

Table 27 provides 235 compounds of formula (I) where Het is

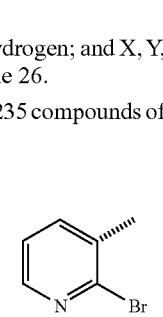

$R^2$ and $R^3$ are both hydrogen; and X, Y, $R^1$, $R^4$, $R^5$, $R^6$ and $R^7$ are as defined in Table 27.

Table 28 provides 235 compounds of formula (I) where Het is

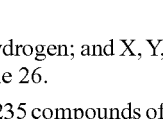

$R^2$ and $R^3$ are both hydrogen; and X, Y, $R^1$, $R^4$, $R^5$, $R^6$ and $R^7$ are as defined in Table 28.

Table 29 provides 235 compounds of formula (I) where Het is

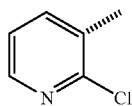

$R^2$ and $R^3$ are both hydrogen; and X, Y, $R^1$, $R^4$, $R^5$, $R^6$ and $R^7$ are as defined in Table 29.

Throughout this description, temperatures are given in degrees Celsius; "NMR" means nuclear magnetic resonance spectrum; MS stands for mass spectrum; and "%" is percent by weight, unless corresponding concentrations are indicated in other units; "syn" refers to a syn configuration of the relevant substituent with respect to the annellated benzene ring; and "anti" refers to an anti configuration of the relevant substituent with respect to the annellated benzene ring.

The following abbreviations are used throughout this description:
m.p.=melting point b.p.=boiling point.
s=singlet br=broad
d=doublet dd=doublet of doublets
t=triplet q=quartet
m=multiplet ppm=parts per million Table 30 shows selected melting point and selected NMR data, all with $CDCl_3$ as the solvent (unless otherwise stated; if a mixture of solvents is present, this is indicated as, for example, [$CDCl_3/d_6$-DMSO]), (no attempt is made to list all characterising data in all cases) for compounds of Tables 1 to 29.

TABLE 30

| Compound No. | m.p (/° C.) | NMR proton shifts (/ppm) ($CDCl_3$ unless otherwise stated) |
|---|---|---|
| 1.01 | 92-96 | 6.85 and 6.7 (two m, 2 × 2H), 6.47 (t, 1H), ca.5-3 (br., exchangeable with $D_2O$, 2H), 2.07 (s, 3H), 1.85 (s, 3H). |
| 1.10 | 121-124 | |
| 2.01 | 92-93 | 7.05 (t, 1H), 6.7 (t, 2H), ca.5 (brd, exchangeable with $D_2O$, 2H), 2.0 (s, 3H), 1.9 (m, 2H), 1.8 (s, 3H), 1.7 (m, 1H), 1.5 (m, 1H). |
| 2.02 | 92-93 | |
| 2.03 | 112-114 | |
| 2.10 | 75-76 | |
| 2.16 | 63-64 | 6.90 (dd (~t), $J_1$ = 7.3 Hz, $J_2$ = 8.2 Hz, 1H), 6.65 (d, J = 7.3 Hz, 1H), 6.46 (d, J = 8.2 Hz, 1H), 3.46 (br., exchangeable with $D_2O$, 2H), 3.35 (br.s, 1H), 3.31 (br.s, 1H), 1.87 (m, 2H), 1.70 (m, 1H), 1.50 (m, 1H), 1.18 (m, 1H). |
| 2.23 | 74-75 | 6.99 (t, 1H), 6.63 (d overlapped by a t, 2H), 4.0-3.5 (br, exchangeable with $D_2O$, 2H), 3.08 (br. s, 1H), 2.94 (br.s, 1H), 1.76 (m, 4H), 1.40 (m, 4H). |
| 2.53 | 139-140 | 6.97 (t, 1H), 6.69 (d, 1H), 6.51 (d, 1H), 4.12 (br s, 1H), 4.03 (br s, 1H), 3.9-3.1 (br, exchangeable with $D_2O$, 2H), 2.06 (s, 3H) overlapped by a m at 2.12-2.05 (2H), 1.26-1.19 (m, 2H). |
| 2.55 | viscous | 6.95 (t, 1H), 6.68 (d, 1H), 6.51 (d, 1H), 4.26 (d, 1H), 4.18 (d, 1H), 3.56 (br, exchangeable with $D_2O$, 2H), 2.22 (br d, 2H), 2.10 (br, 2H), 1.22 (m, 2 + 2H), 1.03 (t, 3H). |
| 2.58 | 89-90 | 6.94 (dd (~t), $J_1$ = 7.3 Hz, $J_2$ = 7.9 Hz, 1H), 6.68 (d, J = 7.3 Hz, 1H), 6.49 (d, J = 7.9 Hz, 1H), 5.11 (br, 1H), 5.04 (br, 1H), 3.5-3.0 (br, exchangeable with $D_2O$), 2.07 (m, 2H), 1.40 (s, 9H), 1.30 (m, 2H). |
| 2.59 | oil | 6.91 (dd (~t), $J_1$ = 7.3 Hz, $J_2$ = 7.9 Hz, 1H), 6.66 (d, J = 7.3 Hz, 1H), 6.44 (d, J = 7.9 Hz, 1H), 4.55 (d, J = ~1 Hz, 1H)), 4.48 (d, J = ~1 Hz, 1H), 4.0-3.0 (br, exchangeable with $D_2O$, H), 2.02 (m, 2H), 1.25 (m, 2H). |
| 2.61 | 176-177 | syn-anti-mixture: 8.00 & 7.98 (s, 1H), 6.96 (t, 1H), 6.71 & 6.67 (d, 1H), 6.50 (d, 1H), 5.55 & 5.48 (br s, 1H), 5.09 & 5.02 (br s, 1H), 4.0-3.0 (br, exchangeable with $D_2O$, 2H), 2.06 (m, 2H), 1.37-1.47 (m, 2H). |
| 2.64 | 110-111 | 6.96 (t, 1H), 6.58 (d, 1H), 6.47 (d, 1H), 3.79 (br, 2H), 2.29 (s, 3H), 2.01 (s, 6H), 1.98 (m, 2H), 1.54 (m, 1H), 1.32 (m, 1H). |
| 2.65 | 94-95 | 6.96 (t, 1H), 6.59 (d, 1H), 6.47 (d, 1H), ca 3.7 (br, exchangeable with $D_2O$, 2H), 2.18 (s, 3H), 1.95 (m, 2H), 1.93 (s, 3H), 1.49 (m, 1H), 1.37 (s, 9H), 1.25 (m, 1H). |
| 2.67 | 104-105 | 6.96 (t, 1H), 6.69 (d), 1H), 6.50 (d, 1H), 5.20 (br, 1H), 5.13 (br, 1H), 3.64 (s, 3H), 2.10 (m, 2H), 1.33 (m, 2H). |
| 2.73 | 114-115 | 6.97 (t, 1H), 6.60 (d, 1H), 3.80 (br, 2H), 3.55 (s, 3H), 2.20 (s, 3H), 1.97 (m, 2H), 1.95 (s, 3H), 1.50 (m, 1H), 1.29 (m, 1H). |
| 2.75 | viscous | 6.95 (t, 1H), 6.70 (d, 1H), 6.50 (d, 1H), 5.20 (br, 1H), 5.13 (br, 1H), 4.07 (q, 2H), 3.33 (br, 2H), 2.10 (m, 2H), 1.32 (m, 2H), 1.22 (t, 3H). |
| 2.77 | viscous | 6.97 (t, 1H), 6.72 (d, 1H), 6.53 (d, 1H), 5.24 (m, 1H), 5.16 (m, 1H), 4.27 (br, 2H), 3.64 (t, 2H), 3.18 (br, 2H), 2.12 (m, 2H), 1.35 (m, 2H). |

TABLE 30-continued

| Compound No. | m.p (/° C.) | NMR proton shifts (/ppm) (CDCl$_3$ unless otherwise stated) |
|---|---|---|
| 2.79 | viscous | 6.96 (t, 1H), 6.71 (d, 1H), 6.52 (d, 1H), 5.20 (br, 1H), 5.12 (br, 1H), 4.02 (t, 2H), 3.19 (br, 2H), 2.09 (m, 2H), 1.57 (m, 2H), 1.34 (m, 4H), 0.91 (t, 3H). |
| 2.81 | viscous | 6.96 (t, 1H), 6.71 (d, 1H), 6.52 (d, 1H), 5.21 (br, 1H), 5.13 (br, 1H), 3.80 (d, 2H), 3.25 (br, 2H), 2.10 (m, 2H), 1.88 (m, 1H), 1.33 (m, 2H), 0.89 (d, 6H). |
| 2.82 syn:anti = 86:14 | waxy solid | data for the syn component: 6.91 (t, 1H), 6.65 (d, 1H), 6.49 (d, 1H), 3.5 (br, 2H), 3.20 (br, 1H), 3.15 (br, 1H), 1.92 (m, 2H), 1.54 (d, 1H), 1.19 (m, 2H), 1.03 (m, 2H), 0.81 (d, 6H). |
| 2.82 syn:anti = 35:65 | oil | data for the syn-anti mixture: 6.94-6.87 (m, 1H), 6.65 (m, 1H), 6.52 and 6.46 (d, 1H), 3.52 (br, 2H), 3.21, 3.16 and 3.14 (three m, 2H), 1.96-1.84 (m, 2H), 1.55 and 1.49 (two d, 1H), 1.43 and 1.03 (m, 1H), 1.22-1.12 (m, 2H), 0.92 and 0.82 (two m, 6H). |
| 2.84 syn:anti = 12:88 | viscous | data for the anti component: 6.89 (t, 1H), 6.64 (d, 1H), 6.48 (d, 1H), ca 4.0-3.75 (br, 2H), 3.03 (br, 1H), 3.00 (br, 1H), 1.96-1.87 (m, 3H), 1.58 (m, 1H), 1.12 (m, 3H), 0.91 (d, 6H). |
| 2.84 syn:anti = 82:18 | viscous | data for the syn component: 6.92 (t, 1H), 6.64 (d, 1H), 6.50 (t, 1H), 3.53 (br, 2H), 3.08 (m, 1H), 3.03 (m, 1H), 2.02 (t, 1H), 1.90 (m, 2H), 1.46 (m, 1H), 1.16 (m, 2H), 0.92 (m, 2H), 0.81 (d, 6H). |
| 2.86 | viscous | 6.92 (t, 1H), 6.66 (d, 1H), 6.49 (d, 1H), 3.52 (br, 2H), 2.62 (m, 1H), 2.59 (m, 1H), 2.07 (m, 2H), 1.27 (m, 2H), 0.54 (m, 2H), 0.45 (m, 2H). |
| 2.88 syn:anti = 46:54 | viscous | data for the syn-anti-(1:1) mixture: 6.91 and 6.89 (two t, 1H), 6.63 (d, 1H), 6.48 and 6.46 (two d, 1H), 3.52 (br, 2H), 3.20, 3.16 and 3.13 (three, m, 2H), 1.93-1.86 (m, 2H), 1.78 and 1.72 (two d, 1H), 1.45 (m, 1H), 1.37-1.11 (m, 6H), 0.85 and 0.76 (two m, 6H). |
| 2.89 syn:anti = 84:16 | viscous | data for the syn component: 6.90 (t, 1H), 6.64 (d, 1H), 6.48 (d, 1H), 3.51 (br, 2H), 3.19 (br s, 1H), 3.13 (br s, 1H), 2.08 (t, 1H), 1.94 (m, 2H), 1.20 (m, 2H), 0.97 (m, 1H), 0.90 (m, 1H), 0.57 (1H), 0.35 (m, 2H), 0.13 (m, 2H). |
| 2.90 syn:anti = 74:26 | viscous | data for the syn component: 6.91 (t, 1H), 6.64 (d, 1H), 6.49 (d, 1H), 3.52 (br, 2H), 3.12 (br s, 1H), 3.08 (br s, 1H), 1.91 (m, 2H), 1.8-1.0 (m, 12H). |
| 2.94 syn:anti = 74:26 | viscous | data for the syn component: 7.28 (m, 2H), 7.17 (m, 1H), 7.04 (d, 2H), 6.99 (t, 1H), 6.72 (d, 1H), 6.57 (d, 1H), 3.6 (br, 2H), 3.06 (m, 2H), 2.35 (m, 2H), 2.20 (m, 2H), 1.89 (m, 2H), 1.20 (m, 2H). |
| 2.106 | 81-82 | 6.90 (t, 1H), 6.67 (d, 1H), 6.47 (d, 1H), 3.77 (m, 1H), 3.73 (m, 1H), 3.56 (br, 2H), 1.88 (m, 2H), 1.63 (s, 6H), 1.26 (m, 2H). |
| 2.107 | viscous | 6.89 (t, 1H), 6.65 (d, 1H), 6.46 (d, 1H), 3.76 (m, 1H), 3.72 (m, 1H), 3.56 (br, 2H), 2.12-1.90 (m, 4H), 1.88 (m, 2H), 1.26 (m, 2H), 0.94 (m, 6H). |
| 3.001 | 150-154 | |
| 3.002 | 163-165 | |
| 3.023 | 129-133 [as a mixture of rotational isomers] | 7.62 (br), 7.44 (d, J ~1 Hz), 7.32 (d, J ~1 Hz), 7.2 (m), 7.0 (m); these signals account for 6 protons. Further signals at 3.7 (s, 3H), 1.84 (s, 3H), 1.82 (s, 3H), 2.0-1.5 (m, 4H). |
| 3.024 | 172-176 | 7.5-7.0 (m) and 6.8 (br.s) accounting for 5H, 5.7-4.8 (two sets of AB systems, 2H), 4.1 (m, 1H), 3.35 and 3.3 (two s, accounting for 3H), 1.85, 1.75, 1.70 (three s, accounting for 6H), 2.0-1.4 (m, 4H). |
| 3.027 | amorphous solid | 7.60 br.s, 1H), 7.34 (br.s, 1H), 7.22-7.07 (m, 3H), 7.01 (br.s, 1H), 5.27 (d, 1H), 3.71 (s, 3H), 2.19 (m, 1H), 1.91 (m, 1H), 1.83 (s, 3H), 1.71 (m, 1H), 1.49 (m, 1H). |
| 3.028 | amorphous solid | 7.68 (br., 1H), 7.53 (d, 1H), 7.37 (br.s, 1H), 7.17 (t, 1H), 7.00 (br.s, 1H), 6.96 (d, 1H), 5.39 (d, 1H), 3.70 (s, 3H), 2.25 (m, 1H), 1.83 (s, 3H), 1.83-1.66 (m, 2H), 1.48 (m, 1H). |
| 3.035 | amorphous solid | |
| 3.048 | amorphous solid | 7.85 (d, 1H), 7.72 (br., 1H), 7.48 (br.s, 1H), 7.60 (t, 1H), 7.0 (br s, 1H), 9.95 (d, 1H), 3.73 (s, 3H), 3.43 (br.s, 1H), 3.37 (br.s, 1H), 1.9 (m, 2H), 1.75 (m, 1H), 1.55 (m, 1H), 1.2 (m, 2H). |
| 3.052 | 136-138 | |
| 3.076 | 154-155 | |
| 3.152 | amorphous solid | 7.71 (br, 1H), 7.69 (d, 1H), 7.39 (br s, 1H), 7.18 (t, 1H), 7.06 (d, 1H), 6.99 (br s, 1H), 4.30 (br s, 1H), 4.18 (br s, |

TABLE 30-continued

| Compound No. | m.p (/° C.) | NMR proton shifts (/ppm) (CDCl$_3$ unless otherwise stated) |
|---|---|---|
| | | 1H), 3.71 (s, 3H), 2.20 (m, 2H), 2.12 (s, 3H), 1.42-1.21 (m, 2H).. |
| 3.162 | amorphous solid | 7.71 (d, 1H), 7.68 (br, 1H), 7.39 (br s, 1H), 7.17 (t, 1H), 7.05 (d, 1H), 7.01 (br s, 1H), 4.40 (br s, 1H), 4.28 (br s, 1H), 3.72 (s, 3H), 2.24 (br, 2H), 2.17 (br, 2H), 1.37 (t, 1H), 1.25 (t, 1H), 1.04 (t, 3H). |
| 3.168 | amorphous solid | 7.71 (br, 2H), 7.37 (br.s, 1H), 7.14 (t, 1H), 7.05 (d, 1H), 7.00 (br.s, 1H), 5.18 (br, 1H), 5.11 (br, 1H), 3.71 (s, 3H), 2.14 (m, 2H), 1.50 (m, 1H), 1.38 (s, 9H), 1.30 (m, 1H). |
| 3.172 | amorphous solid | syn-anti mixture: 8.00 (s, 1H), 7.72 (br, 1H), 7.58 & 7..31 (d, 1H), 7.38 & 7.36 (br s, 1H), 7.16 (t, 1H), 7.11 & 7.09 (d, 1H), 7.01 (br s, 1H), 5.61 & 5.53 (br s, 1H), 5.19 & 5.09 (br s, 1H), 3.71 (s, 3H), 2.11 (m, 2H), 1.75-1.61 (m, 1H), 1.50-1.39 (m, 1H). |
| 3.176 | 231-232 | 7.48 (br, 1H), 7.22 (t, 1H), 7.09 (br, 1H), 7.06 (d, 1H), 6.96 (br s, 1H), 5.91 (br s, 1H), 3.69 (s, 3H), 2.87 (m, 1H), 2.22 (m, 2H), 1.97 (s, 3H), ca 1.9 (m, 1H), 1.66 (s, 3H), 1.49 (s, 3H). |
| 3.183 | amorphous solid | 7.71 (br, 1H), 7.3 (br d, 1H), 7.38 (br s, 1H), 7.16 (t, 1H), 7.06 (d, 1H), 7.02 (br s, 1H), 5.25 (m, 1H), 5.18 (m, 1H), 3.72 (s, 3H), 3.62 (s, 3H), 2.16 (m, 2H), 1.55 (m, 1H), 1.35 (m, 1H). |
| 3.189 | amorphous | 7.65 (br, 1H), 7.31 (d, 1H), 7.30 (br s, 1H), 7.17 (t, 1H), 7.02 (d, 1H), 7.01 (br s, 1H), 3.72 (s, 3H), 3.54 (s, 3H), 2.08 (s, 3H), 1.99 (s, 3H), 1.94 (m, 2H), 1.76 (m, 1H), 1.33 (m, 1H). |
| 3.191 | amorphous | 7.72 (br, 1H), 7.64 (d, 1H), 7.38 (br s, 1H), 7.16 (t, 1H), 7.07 (d, 1H), 7.02 (br s, 1H), 5.26 (m, 1H), 5.20 (m, 1H), 4.05 (q, 1H), 3.72 (s, 3H), 2.15 (m, 2H), 1.55 (m, 1H), 1.35 (m, 1H), 1.20 (t, 3H). |
| 3.193 | amorphous | 7.72 (br, 1H), 7.60 (d, 1H), 7.38 (br s, 1H), 7.16 (t, 1H), 7.08 (d, 1H), 7.02 (br s, 1H), 5.29 (m, 1H), 5.22 (m, 1H), 4.24 (m, 2H), 3.73 (s, 3H), 3.61 (t, 2H), 2.18 (m, 2H), 1.59 (m, 1H), 1.37 (m, 1H). |
| 3.195 | amorphous | 7.72 (br, 1H), 7.65 (d, 1H), 7.38 (br s, 1H), 7.15 (t, 1H), 7.06 (d, 1H), 7.01 (br s, 1H), 5.26 (m, 1H), 5.18 (m, 1H), 4.00 (t, 2H), 3.72 (s, 3H), 2.15 (m, 2H), 1.55 (m, 3H), 1.34 (m, 3H), 0.89 (t, 3H). |
| 3.197 | amorphous | 7.72 (br, 1H), 7.66 (d, 1H), 7.38 (br s, 1H), 7.16 (t, 1H), 7.07 (d, 1H), 7.01 (br s, 1H), 5.27 (m, 1H), 5.19 (m, 1H), 3.78 (dd, 2H), 3.73 (s, 3H), 2.16 (m, 2H), 1.87 (m, 1H), 1.55 (m, 1H), 1.35 (m, 1H). |
| 3.202 syn:anti = 90:10 | 121-125 | data for the syn component: 7.91 (d, 1H), 7.72 (br, 1H), 7.38 (br s, 1H), 7.10 (t, 1H), 7.00 (br s, 1H), 6.97 (d, 1H), 3.72 (s, 3H), 3.32 (m, 1H), 3.22 (m, 1H), 1.95 (m, 2H), 1.58 (d, 1H), 1.20 (m, 2H), 0.90 (m, 1H), 0.81 (m, 6H). |
| 3.202 syn:anti = 34:66 | amorphous | data for the syn-anti mixture: 7.91 and 7.85 (two d, 1H), 7.72 (br, 1H), 7.37 (m, 1H), 7.12-7.05 (m, 1H), 6.99 (m, 1H), 6.98-6.94 (m, 1H), 3.71 (s, 3H), 3.32, 3.25. 3.22 and 3.19 (four m, 2H), 1.96-1.88 (m, 2H), 1.58 and 1.51 (two d, 1H), 1.44 and 0.98 (two m, 1H), 1.26-1.12 (m, 2H). 0.91 and 0.81 (two m, 6H). |
| 3.208 syn:anti = 10:90 | 130-131 | data for the anti component: 7.85 (d, 1H), 7.70 (br, 1H), 7.38 (br s, 1H), 7.08 (t, 1H), 6.99 (br s, 1H), 6.95 (d, 1H), 3.71 (s, 3H), 3.12 (m, 1H), 3.06 (m, 1H), 2.0-1.9 (m, 3H), 1.6-1.5 (m, 2H), 1.22-1.11 (m, 3H), 0.92 (d, 6H). |
| 3.208 syn:anti = 85:15 | amorphous | data for the syn component: 7.92 (d, 1H), 7.70 (br, 1H), 7.38 (br s, 1H), 7.11 (t, 1H), 6.99 (br s, 1H), 6.96 (d, 1H), 3.71 (s, 1H), 3.19 (m, 1H), 3.10 (m, 1H), 2.06 (t, 1H), 1.97 (m, 2H), 1.44 (m, 1H), 1.27-1.11 (m, 2H), 0.90 (m, 2H), 0.79 (d, 6H). |
| 3.210 | 155-157 | 7.84 (d, 1H), 7.68 (br, 1H), 7.37 (br s, 1H), 7.11 (t, 1H), 6.98 (d, 1H), 3.71 (s, 3H), 2.69 (m, 1H), 2.65 (m, 1H), 2.09 (m, 2H), 1.33 (m, 1H), 1.32 (m, 1H), 0.49 (m, 4H). |
| 3.212 | amorphous | data for the syn-anti mixture: 7.92 and 7.85 (two d, 1H), 7.72 (br, 1H), 7.38 (m, 1H), 7.13-7.06 (m, 1H), 7.00 (m, 1H), 6.96 (m, 1H), 3.72 (s, 3H), 3.32, 3.25, 3.22 and 3.19 (four m, 2H), 1.92 (m, 2H), 1.82 and 1.72 (two d, 1H), 1.43 (m, 1H), 1.35-1.05 (m, 6H), 0.84 and 0.73 (two t, 6H). |
| 3.213 syn:anti = 95:05 | 115-117 | data for the syn component: 7.90 (d, 1H), 7.71br, 1H), 7.38 (br s, 1H), 7.10 (t, 1H), 6.99 (br s, 1H), 6.96 (d, 1H), 3.71 (s, 3H), 3.31 (m, 1H), 3.18 (m, 1H), 2.12 (t, 1H), 1.98 (m, 2H), 1.28-1.14 (m, |

TABLE 30-continued

| Compound No. | m.p (/° C.) | NMR proton shifts (/ppm) (CDCl₃ unless otherwise stated) |
|---|---|---|
| | | 3H), 1.0-0.78 (m, 2H), 0.55 (m, 1H), 0.34 (m, 2H), 0.16 (m, 2H). |
| 3.214 syn:anti = 74:26 | amorphous | data for the syn component: 7.93 (d, 1H), 7.72 (br, 1H), 7.38 (br s, 1H), 7.11 (t, 1H), 7.00 (br s, 1H), 6.95 (d, 1H), 3.71 (s, 3H), 3.24 (m, 1H), 3.14 (m, 1H), 1.94 (m, 2H), 1.8-0.88 (m, 12H). |
| 3.218 syn:anti = 92:08 | 143-146 | data for for the syn component: 7.96 (d, 1H), 7.70 (br, 1H), 7.37 (br s, 1H), 7.30-6.95 (m, 8H), 3.72 (s, 3H), 3.18 (m, 1H), 3.12 (m, 1H), 2.37-2.07 (m, 3H), 1.93 (m, 2H), 1.25 (m, 2H). |
| 3.230 | amorphous | 7.82 (d, 1H), 7.75 (br, 1H), 7.39 (br s, 1H), 7.08 (t, 1H), 7.01 (br s, 1H), 6.98 (d, 1H), 3.83 (m, 1H), 3.78 (m, 1H), 3.72 (s, 3H), 1.90 (m, 2H), 1.61 (s, 6H), 1.35-1.21 (m, 2H). |
| 3.231 | amorphous | 7.81 (d, 1H), 7.75 (br, 1H), 7.38 (br s, 1H), 7.08 (t, 1H), 7.00 (br s, 1H), 6.97 (d, 1H), 3.85 (m, 1H), 3.77 (m, 1H), 3.72 (s, 3H), 2.1-1.9 (m, 6H), 1.38-1.21 (m, 2H), 0.93 (m, 6H). |
| 4.048 | viscous oil | 7.87 (br, 1H), 7.80 (d, 1H), 7.27 (m, 1H), 7.07 (t, 1H), 6.96 (d, 1H), 6.95 (t, J = 56 Hz, 1H), 6.87 (m, 1H), 3.68 (s, 3H), 3.47 (br.s, 1H), 3.36 (br.s, 1H), 1.90 (m, 2H), 1.74 (m, 1H), 1.50 (m, 1H), 1.16-1.24 (m, 2H). |
| 8.048 | viscous oil | 7.83 (br d, 1H), 7.76 (br, 1H), 7.55 (br s, 1H), 7.12 (br s, 1H), 7.09 (t, 1H), 6.98 (d, 1H), 5.19 (s, 2H), 3.45 (br s, 1H), 3.37 (br s, 1H), 3.32 (s, 3H), 1.92 (m, 2H), 1.77 (m, 1H), 1.52 (m, 1H), 1.22 (m, 2H). |
| 11.048 | viscous oil | 7.90 (br d, 1H), 7.73 (br, 1H), 7.09 (t, 1H), 7.04 (br s, 1H), 6.98 (d, 1H), 3.68 (s, 3H), 3.43 (br s, 1H), 3.38 (br s, 1H), 1.90 (m, 2H), 1.77 (m, 1H), 1.52 (m, 1H), 1.24 (m, 2H). |
| 14.002 | 148-151 | |
| 14.023 | 162-166 | |
| 14.024 | 148-150 | |
| 14.027 | 182-184 | |
| 14.028 | amorphous solid | 8.04 (s, 1H), 7.66 (br., 1H), 7.45 (d, 1H), 7.19 (t, 1H), 6.99 (d, 1H), 5.37 (d, 1H), 3.98 (s, 3H), 2.25 (m, 1H), 1.83 (s, 3H), 1.83-1.65 (m, 2H), 1.47 (m, 1H). |
| 14.035 | 144-146 | |
| 14.048 | amorphous solid | 8.05 (s, 1H), 7.8 (d, 1H), 7.7 (br.s, 1H), 7.6 (t, 1H), 7.0 (d, 1H), 3.98 (s, 3H), 3.43 (br.s, 1H), 3.39 (br.s, 1H), 1.9 (m, 2H), 1.75 (m, 1H), 1.54 (m, 1H), 1.2 (m, 2H). |
| 14.052 | 121-122 | |
| 14.076 | 127-130 | |
| 14.152 | amorphous solid | 8.09 (s, 1H), 7.75 (br, 1H), 7.62 (d, 1H), 7.19 (t, 1H), 7.09 (d, 1H), 4.30 (br, 1H), 4.20 (br s, 1H), 3.98 (s, 3H), 2.2-2.1 (m, 2H), 2.11 (br s, 3H), 1.4-1.2 (m, 2H). |
| 14.162 | 142-147 | 8.09 (s, 1H), 7.74 (br, 1H), 7.63 (d, 1H), 7.19 (t, 1H), 7.08 (d, 1H), 4.40 (br s, 1H), 4.31 (br s, 1H), 4.00 (s, 3H), 2.26 (br, 2H), 2.15 (br, 2H), 1.38 (t, 1H), 1.26 (t, 1H), 1.05 (t, 3H). |
| 14.168 | amorphous solid | 8.04 (s, 1H), 7.72 (br, 1H), 7.60 (d, 1H), 7.16 (t, 1H), 7.08 (d, 1H), 5.15 (br, 1H), 5.12 (br, 1H), 3.99 (s, 3H), 2.13 (m, 2H), 1.49 (m, 1H), 1.38 (s, 9H), 1.32 (m, 1H). |
| 14.172 | 123-124 | syn-anti mixture; DMSO: 9.97 (s, 1H), 8.45 & 8.43 (br, 1H), 7.87 (br s, 1H), 7.21 & 7.12 (d, 1H), 7.06 (m, 2H), 5.42 & 5.29 (br, 1H), 5.24 (m, 1H), 3.88 (s, 3H), 1.87 (m, 2H), 1.45 & 1.39 (m, 1H), 1.21 (m, 1H). |
| 14.176 | 232-233 | 8.12 (br, 1H), 7.23 (t, 1H), 7.09-7.05 (m, 2H), 5.93 (s, 1H), 3.97 (s, 3H), 2.90 (m, 1H), 2.32-2.20 (m, 2H), 1.97 (s, 3H), 1.90 (m, 1H), 1.67 (s, 3H), 1.48 (s, 3H). |
| 14.178 | 148-150 | 7.98 (br, 1H), 7.67 (br, 1H), 7.30 (d, 1H), 7.19 (t, 1H), 7.04 (d, 1H), 3.99 (s, 3H), 2.05 (s, 3H), 1.97 (s, 3H) overlapped by a m (2.00-1.89, 2H), 1.68 (m, 1H), 1.35 (s, 9H), 1.31 (m, 1H). |
| 14.183 | amorphous solid | 8.05 (s, 1H), 7.74 (br, 1H), 7.53 (d, 1H), 7.17 (t, 1H), 7.10 (d, 1H), 5.23 (m, 1H), 5.19 (m, 1H), 4.00 (s, 3H), 3.62 (s, 3H), 2.14 (m, 2H), 1.55 (m, 1H), 1.35 (1H). |
| 14.189 | amorphous | 7.99 (br s, 1H), 7.68 (br, 1H), 7.28 (d, 1H), 7.19 (t, 1H), 7.06 (d, 1H), 3.99 (s, 3H), 3.54 (s, 3H), 2.06 (s, 3H), 2.02-1.91 (m, 2H), 1.72 (m, 1H), 1.35 (m, 1H). |
| 14.191 | amorphous | 8.05 (s, 1H), 7.75 (br, 1H), 7.55 (d, 1H), 7.17 (t, 1H), 7.11 (d, 1H), 5.23 (m, 1H), 5.20 (m, 1H), 4.05 (q, 2H), 4.00 (s, 3H), 2.15 (m, 2H), 1.54 (m, 1H), 1.35 (m, 1H), 1.20 (t, 3H). |
| 14.193 | amorphous | 8.05 (s, 1H), 7.72 (br, 1H), 7.52 (d, 1H), 7.18 (t, 1H), 7.12 (d, 1H), 5.27 (m, 1H), 5.23 (m, 1H), 4.24 (m, 2H), 4.00 (s, 3H), 3.61 (t, 2H), 2.19 (m, 2H), 1.58 (m, 1H), 1.38 (m, 1H). |

TABLE 30-continued

| Compound No. | m.p (/° C.) | NMR proton shifts (/ppm) (CDCl₃ unless otherwise stated) |
|---|---|---|
| 14.195 | amorphous | 8.05 (s, 1H), 7.75 (br, 1H), 7.55 (d, 1H), 7.17 (t, 1H), 7.10 (d, 1H), 5.23 (m, 1H), 5.20 (m, 1H), 4.00 (s, 3H), 4.00 (t, 2H), 2.15 (m, 2H), 1.55 (m, 3H), 1.35 (m, 3H), 0.89 (t, 3H). |
| 14.197 | amorphous | 8.05 (s, 1H), 7.77 (br, 1H), 7.55 (d, 1H), 5.24 (m, 1H), 5.20 (m, 1H), 3.99 (s, 3H), 3.78 (dd, 2H), 2.17 (m, 2H), 1.86 (m, 1H), 1.55 (m, 1H), 1.36 (m, 1H), 0.87 (d, 6H). |
| 14.202 syn:anti = 90:10 | 145-150 | data for the syn component: 8.06 (s, 1H), 7.84 (d, 1H), 7.70 (br, 1H), 7.12 (t, 1H), 7.01 (d, 1H), 3.99 (s, 3H), 3.29 (m, 1H), 3.23 (m, 1H), 1.96 (m, 2H), 1.60 (d, 1H), 1.20 (m, 2H), 0.96 (m, 1H), 0.80 (m, 6H). |
| 14.202 syn:anti = 28:72 | amorphous | data for the syn-anti mixture: 8.05 (br, 1H), 7.83 and 7.78 (two d, 1H), 7.70 (br, 1H), 7.14-7.07 (m, 1H), 7.01-6.98 (m, 1H), 3.99 (s, 3H), 3.30 and 3.21 (two m, 2H), 1.97-1.90 (m, 2H), 1.60 and 1.51 (two d, 1H), 1.43 and 0.98 (two m, 1H), 1.26-1.12 (m, 2H), 0.91 and 0.82 (two m, 6H). |
| 14.208 syn:anti = 10:90 | 132-133 | data for the anti component: 8.04 (s, 1H), 7.77 (d, 1H), 7.68 (br, 1H), 7.09 (t, 1H), 6.99 (d, 1H), 3.99 (s, 3H), 3.08 (m, 2H), 2.0-1.91 (m, 3H), 1.63-1.55 (m, 2H), 1.22-1.10 (m, 3H), 0.91 (d, 6H). |
| 14.208 syn:anti = 85:15 | 130-133 | data for the syn component: 8.05 (br s, 1H), 7.84 (d, 1H), 7.68 (br, 1H), 7.12 (t, 1H), 7.00 (d, 1H), 3.99 (s, 3H), 3.16 (m, 1H), 3.12 (m, 1H), 2.10 (t, 1H), 1.97 (m, 2H), 1.44 (m, 1H), 1.22 (m, 2H), 0.91 (m, 2H), 0.80 (d, 6H). |
| 14.210 | 151-153 | 8.04 (br, 1H), 7.76 (d, 1H), 7.65 (br, 1H), 7.12 (t, 1H), 7.02 (d, 1H), 3.98 (s, 3H), 2.66 (m, 2H), 2.10 (m, 2H), 1.29 (m, 2H), 0.49 (m, 4H). |
| 14.212 syn:anti = 48:52 | amorphous | data for the syn-anti mixture: 8.05 (br, 1H), 7.84 and 7.78 (two d, 1H), 7.69 (br, 1H), 7.14-7.08 (m, 1H), 6.99 (m, 1H), 3.99 (s, 3H), 3.29, 3.24 and 3.20 (three m, 2H), 1.95 (m, 2H), 1.83 and 1.74 (two d, 1H), 1.44 (m, 1H), 1.35-1.11 (m, 6H), 0.85 and 0.74 (two t, 6H). |
| 14.213 syn:anti = 90:10 | amorphous | data for the syn component: 8.05 (s, 1H), 7.83 (d, 1H), 7.70 (br, 1H), 7.12 (t, 1H), 7.00 (d, 1H), 3.99 (s, 3H), 3.29 (m, 1H), 3.20 (m, 1H), 2.14 (t, 1H), 2.00 (m, 2H), 1.16 (m, 2H), 1.02-0.78 (m, 2H), 0.55 (m, 1H), 0.35 (m, 2H), −016 (m, 2H). |
| 14.214 syn:anti = 74:26 | amorphous | data for the syn component: 8.05 (s, 1H), 7.85 (d, 1H), 7.69 (br, 1H), 7.12 (t, 1H), 7.00 (d, 1H), 3.99 (s, 3H), 3.21 (m, 1H), 3.16 (m, 1H), 1.96 (m, 2H), 1.80-0.0.9 (m, 12H). |
| 14.218 syn:anti = 78:22 | amorphous | data for the syn component: 8.05 (s, 1H), 7.89 (d, 1H), 7.68 (br, 1H), 7.30-6.92 (m, 7H), 4.00 (s, 3H), 3.14 (m, 2H), 2.60-2.10 (m, 3H), 1.94 (m, 2H), 1.29-1.15 (m, 2H). |
| 14.230 | 183-187 | 8.06 (br s, 1H), 7.74 (d, overlapped by br, 2H), 7.09 (t, 1H), 7.02 (d, 1H), 4.00 (s, 3H), 3.83 (m, 1H), 3.80 (m, 1H), 1.92 (m, 2H), 1.62 (s, 6H), 1.35-1.11 (m, 2H). |
| 14.231 | amorphous | 8.05 (br s, 1H), 7.73 (d, overlapped by br, 2H), 7.09 (t, 1H), 7.01 (d, 1H), 3.99 (s, 3H), 3.82 (m, 1H), 3.79 (m, 1H), 2.1-1.95 (m, 4H), 1.92 (m, 2H), 1.38-1.23 (m, 2H), 0.93 (m, 6H). |
| 15.013 | 139-140 | |
| 15.023 | amorphous solid | 7.99 (s, 1H), 7.93 (br., 1H), 7.22-7.16 (m, 2H), 7.03 (d, 1H), 6.88 (t, $J_{HF}$ = 54 Hz, 1H), 3.93 (s, 3H), 1.90 (m, 2H), 1.82 (s, 3H), 1.80 (s, 3H), 1.55 (m, 2H). |
| 15.027 | 168-169 | |
| 15.028 | 145-147 | |
| 15.035 | 136-139 | |
| 15.048 | 132-134 | 8.11 (br., 1H), 8.03 (s, 1H), 7.83 (d, 1H), 7.08 (t, 1H), 6.98 (d, 1H), 6.88 (t, $J_{HF}$ = 54 Hz, 1H), 3.93 (s, 3H), 3.49 (br.s, 1H), 3.37 (br.s, 1H), 1.91 (m, 2H), 1.74 (m, 1H), 1.51 (m, 1H), 1.22 (m, 2H). |
| 15.049 | 107-108 | |
| 15.050 | 115-117 | |
| 15.052 | 118-122 | |
| 15.076 | 148-150 | |
| 15.086 | amorphous solid | 8.00 (s. 1H), 7.97 (br, 1H), 7.64 (d, 1H), 7.15 (t, 1H), 6.94 (d, 1H), 6.86 (t, $J_{HF}$ = 54.3 Hz, 1H), 3.92 (s, 3H), 3.25 (br. s, 1H), 3.03 (br. s, 1H), 1.94 (m, 2H), 1.8-1.6 (m, 8H). |
| 15.152 | 141-147 (dec.) | 8.07 (br, 1H), 8.05 (s, 1H), 7.76 (d, 1H), 7.18 (t, 1H), 7.06 (d, 1H), 6.87 (t, $J_{HF}$ = 54.2 Hz, 1H), 4.26 (br s, 1H), |

TABLE 30-continued

| Compound No. | m.p (/° C.) | NMR proton shifts (/ppm) (CDCl₃ unless otherwise stated) |
|---|---|---|
| | | 4.12 (br s, 1H), 3.95 (s, 3H), 2.16 (m, 2H), 2.07 (s, 3H), 1.37-1.19 (m, 2H). |
| 15.162 | amorphous solid | 8.17 (br, 1H), 8.09 (s, 1H), 7.72 (d, 1H), 7.20 (t, 1H), 7.07 (d, 1H), 6.90 (t, $J_{HF}$ = 54.2 Hz, 1H), 4.56 (br s, 1H), 4.38 (br s, 1H), 3.96 (s, 3H), 2.32 (br, 2H), 2.23 (br, 2H), 1.42 (t, 1H), 1.30 (t, 1H), 1.08 (t, 3H). |
| 15.168 | viscous | 8.12 (br, 1H), 8.04 (s, 1H), 7.72 (d, 1H), 7.15 (t, 1H), 7.06 (d, 1H), 6.89 (t, $J_{HF}$ = 54 Hz, 1H), 5.22 (br, 1H), 5.11 (br, 1H), 3.05 (s, 3H), 2.12 (m, 2H), 1.53-1.24 (m, 2H), 1.37 (s, 9H). |
| 15.172 | amorphous solid | syn-anti mixture: 8.22 & 8.16 (br, 1H), 8.06 (br s, 1H), 8.00 (s, 1H), 7.58 & 7.42 (d, 1H), 7.17 (t, 1H), 7.10 (d, 1H), 6.93 & 6.91 (t, $J_{HF}$ = 54 Hz, 1H), 5.64 & 5.53 (br s, 1H), 5.21 & 5.10 (br s, 1H), 3.95 (s, 3H), 2.10 (m, 2H), 1.63 (m, 1H), 1.43 (m, 1H). |
| 15.176 | 223-224 | |
| 15.183 | amorphous solid | 8.13 (br, 1H), 8.05 (s, 1H), 7.65 (d, 1H), 7.17 (t, 1H), 7.08 (d, 1H), 6.91 (t, $J_{HF}$ = 54 Hz, 1H), 5.29 (br s, 1H), 5.19 (br s, 1H), 3.96 (s, 3H), 3.62 (s, 3H), 2.15 (m, 2H). 1.53 (m, 1H), 1.35 (m, 1H). |
| 15.189 | amorphous | 7.95 (br, 2H), 7.25 (d, 1H), 7.19 (t, 1H), 7.06 (d, 1H), 6.94 (t, $J_{HF}$ = 54 Hz, 1H), 3.94 (s, 3H), 3.54 (s, 3H), 2.07 (s, 3H), 1.99 (s, 3H), 1.98 (m, 2H), 1.72 (m, 1H), 1.35 (m, 1H). |
| 15.191 | amorphous | 8.15 (br, 1H), 8.05 (s, 1H), 7.66 (d, 1H), 7.17 (t, 1H), 7.08 (d, 1H), (6.91 (t, $J_{HF}$ = 54 Hz, 1H), 5.30 (m, 1H), 5.20 (m, 1H), 4.05 (q, 2H), 3.95 (s, 3H), 2.14 (m, 2H), 1.52 (m, 1H), 1.35 (m, 1H), 1.20 (t, 3H). |
| 15.193 | amorphous | 8.12 (br, 1H), 8.05 (s, 1H), 7.64 (d, 1H), 7.18 (t, 1H), 7.09 (d, 1H), 6.91 (t, $J_{HF}$ = 54 Hz, 1H), 5.32 (m, 1H), 5.23 (m, 1H), 4.24 (m, 2H), 3.96 (s, 3H), 3.61 (t, 2H), 2.18 (m, 2H), 1.55 (m, 1H), 1.37 (m, 1H). |
| 15.195 | amorphous | 8.13 (br, 1H), 8.05 (s, 1H), 7.67 (d, 1H), 7.16 (t, 1H), 7.07 (d, 1H), 6.91 (t, $J_{HF}$ = 54 Hz, 1H), 5.29 (M, 1H), 5.18 (m, 1H), 4.01 (t, 2H), 3.95 (s, 3H), 2.16 (m, 2H), 1.53 (m, 3H), 1.33 (m, 3H), 0.88 (t, 3H). |
| 15.197 | amorphous | 8.14 (br, 1H), 8.05 (s, 1H), 7.69 (d, 1H), 7.15 (t, 1H), 7.08 (d, 1H), 6.91 (t, $J_{HF}$ = 54 Hz, 1H), 5.30 (m, 1H), 5.20 (m, 1H), 3.96 (s, 3H), 3.79 (dd, 2H), 2.16 (m, 2H), 1.86 (m, 1H), 1.53 (m, 1H), 1.35 (m, 1H), 0.87 (d, 6H). |
| 15.202 syn:anti = 90:10 | 110-112 | data for the syn component: 8.10 (br, 1H), 8.05 (br s, 1H), 7.92 (d, 1H), 7.11 (t, 1H), 6.98 (d, 1H), 6.87 (t, $J_{HF}$ = 54 Hz, 1H), 3.95 (s, 3H), 3.37 (m, 1H), 3.22 (m, 1H), 1.95 (m, 2H), 1.58 (d, 1H), 1.19 (m, 2H), 0.98 (m, 1H), 0.81 (d, 6H). |
| 15.202 syn:anti = 35:65 | amorphous | data for the syn-anti mixture: 8.09 (br, 1H), 8.04 (br, 1H), 7.91 and 7.84 (two d, 1H), 7.13-7.06 (m, 1H), 7.02-6.96 (m, 1H), 6.88 and 6.87 (two t, $J_{HF}$ = 54 Hz, 1H), 3.95 (s, 3H), 3.38, 3.30, 3.23 and 3.20 (four m, 2H), 1.96-1.89 (m, 2H), 1.58 and 1.50 (two d, 1H), 1.44 and 0.97 (two m, 1H), 1.20-1.12 (m, 2H), 0.91 and 0.82 (two m, 6H). |
| 15.208 syn:anti = 12:88 | viscous | data for the anti component: 8.07 (br, 1H), 8.03 (br s, 1H), 7.84 (d, 1H), 7.08 (t, 1H), 6.97 (d, 1H), 6.88 (t, $J_{HF}$ = 54 Hz, 1H), 3.94 (s, 3H), 3.17 (m, 1H), 3.07 (m, 1H), 1.93 (m, 3H), 1.59 (m, 1H), 1.28-1.12 (m, 4H), 0.91 (d, 6H). |
| 15.208 syn:anti = 93:7 | 117-119 | data for the syn component: 8.08 (br, 1H), 8.04 (br s, 1H), 7.91 (d, 1H), 7.12 (t, 1H), 6.98 (d, 1H), 6.87 (t, $J_{HF}$ = 54 Hz, 1H), 3.94 (s, 3H), 3.25 (m, 1H), 3.11 (m, 1H), 2.07 (t, 1H), 1.96 (m, 2H), 1.45 (m, 1H), 1.19 (m, 2H), 0.89 (m, 2H), 0.80 (d, 6H). |
| 15.210 | 158-160 | 8.04 (br, 2H), 7.84 (d, 1H), 7.12 (t, 1H), 7.00 (d, 1H), 6.86 (t, $J_{HF}$ = 54 Hz, 1H), 3.94 (s, 3H), 2.74 (m, 1H), 2.66 (m, 1H), 2.11 (m, 2H), 1.33 (m, 1H), 1.26 (m, 1H), 0.48 (m, 4H). |
| 15.212 syn:anti = 46:54 | amorphous | data for the syn-anti mixture: 8.09 (br, 1H), 8.04 (br s, 1H), 7.92 and 7.85 (two d, 1H), 7.13-7.07 (m, 1H), 6.98 (m, 1H), 6.88 and 6.87 (two t, $J_{HF}$ = 54 Hz, 1H), 3.95 (s, 3H), 3.37, 3.31, 3.23 and 3.20 (four m, 2H), 1.95 (m, 2H), 1.82 and 1.73 (two d, 1H), 1.46 (m, 1H), 1.37-1.10 (m, 6H), 0.85 and 0.74 (two t, 6H). |
| 15.213 syn:anti = 90:10 | 131-135 | data for the syn component: 8.08 (br, 1H), 8.04 (s, 1H), 7.90 (d, 1H), 7.11 (t, 1H), 6.98 (d, 1H), 6.87 (t, $J_{HF}$ = 54 Hz, 1H), 3.95 (s, 3H), 3.37 (m, 1H), 3.19 (m, 1H), 2.13 (t, 1H), 1.98 (m, 2H), 1.24 (m, 2H), 1.1-0.78 (m, 2H), 0.55 (m, 1H), 0.35 (m, 2H), −0.16 (m, 2H). |

TABLE 30-continued

| Compound No. | m.p (/° C.) | NMR proton shifts (/ppm) (CDCl$_3$ unless otherwise stated) |
|---|---|---|
| 15.214 syn:anti = 74:26 | amorphous | data for the syn component: 8.09 (br, 1H), 8.04 (s, 1H), 7.92 (d, 1H), 7.12 (t, 1H), 6.98 (d, 1H), 6.87 (t, J$_{HF}$ = 54 Hz, 1H), 3.95 (s, 3H), 3.29 (m, 1H), 3.15 (m, 1H), 1.95 (m, 2H), 1.80-0.90 (m, 12H). |
| 15.218 syn:anti = 74:26 | amorphous | data for the syn component: 8.08 (br, 1H), 8.05 (s, 1H), 7.96 (d, 1H), 7.3-6.9 (m, 7H), 6.85 (t, J$_{HF}$ = 54 Hz, 1H), 3.96 (s, 3H), 3.23 (m, 1H), 3.13 (m, 1H), 2.4-2.07 (m, 3H), 1.95 (m, 2H), 1.3-1.1 (m, 2H). |
| 15.230 | amorphous | 8.15 (br, 1H), 8.05 (br s, 1H), 7.83 (d, 1H), 7.09 (t, 1H), 7.00 (d, 1H), 6.90 (t, J$_{HF}$ = 54 Hz, 1H), 3.94 (s, 3H), 3.92 (m, 1H), 3.80 (m, 1H), 1.91 (m, 2H), 1.61 (s, 6H), 1.35-1.22 (m, 2H). |
| 15.231 | amorphous | 8.13 (br, 1H), 8.04 (br s, 1H), 7.82 (d, 1H), 7.09 (t, 1H), 6.99 (d, 1H), 6.90 (t, J$_{HF}$ = 54 Hz, 1H), 3.94 (s, 3H), 3.91 (m, 1H), 3.78 (m, 1H), 2.1-1.95 (m, 4H), 1.91 (m, 2H), 1.39-1.21 (m, 2H), 0.93 (m, 6H). |
| 16.048 | amorphous solid | 8.16 (brd d, 1H), 7.98 (brd s, 1H), 7.85 (d, 1H), 7.10 (t, 1H), 6.99 (d, 1H), 5.72 (AB-signal, 1H), 5.59 (AB-signal, 1H), 3.94 (s, 3H), 3.47 (br s, 1H), 3.38 (brd s, 1H), 1.91 (m, 2H), 1.76 (m, 1H), 1.52 (m, 1H), 1.23 (m, 2H). |
| 16.076 | viscous | 8.13 (brd, 1H), 7.95 (brd s, 1H), 7.70 (d, 1H), 7.19 (t, 1H), 7.02 (d, 1H), 5.64 (d, J$_{HF}$ = 48.7 Hz, 2H), 3.92 (s, 3H), 3.15 (br s, 1H), 3.02 (brd s, 1H), 1.77 (m, 4H), 1.39 (d, 4H). |
| 21.023 | 161-165 | |
| 20.048 | 132-133 | |
| 21.048 | 136-138 | |
| 22.048 | viscous oil | 7.78 (br., 1H), 7.68 (d, 1H), 7.12-7.03 (m, 2H), 3.39 (br.s, 2H), 2.76 (s, 3H), 1.92 (m, 2H), 1.76 (m, 1H), 1.53 (m, 1H), 1.20 (m, 2H). |
| 23.048 | viscous oil | 7.60 (br d, 1H), 7.38 (br, 1H), 7.10 (t, 1H), 7.03 (d, 1H), 3.39 (m, 2H), 2.76 (s, 3H), 1.93 (m, 2H), 1.78 (m, 1H), 1.55 (m, 1H), 1.23 (m, 2H). |
| 24.048 | viscous oil | 7.85 (br., 1H), 7.72 (d, 1H), 7.12-7.02 (m, 2H), 3.43 (br.s, 1H), 3.40 (br.s, 1H), 2.63 (s, 3H), 1.93 (m, 2H), 1.78 (m, 1H), 1.55 (m, 1H), 1.23 (m, 2H). |
| 29.048 | 158-160 | |
| 29.052 | 151-152 | |
| 29.202 syn:anti = 90:10 | 146-147 | data for the syn component: 8.53 (m, 1H), 8.28 (d, 1H), 8.17 (br, 1H), 7.82 (d, 1H), 7.42 (d, 1H), 7.15 (t, 1H), 7.05 (d, 1H), 3.37 (m, 1H), 3.26 (m, 1H), 1.98 (m, 2H), 1.62 (d, 1H), 1.24 (m, 2H), 0.97 (m, 1H), 0.82 (d, 6H). |
| 29.202 syn:anti = 34:66 | amorphous | data for the syn-anti mixture: 8.53 (m, 1H), 8.27 (m, 1H), 8.15 (br, 1H), 7.82-7.77 (m, 1H), 7.42 (m, 1H), 7.17-7.10 (m, 1H), 7.06-7.02 (m, 1H), 3.38, 3.30, 3.26 and 3.23 (four m, 2H), 1.99-1.90 (m, 2H), 1.62 and 1.54 (two d, 1H), 1.46 and 0.99 (two m, 1H), 1.30-1.10 (m, 2H), 0.91 and 0.83 (two m, 6H). |
| 29.208 syn:anti = 82:18 | amorphous | |
| 29.213 syn:anti = 90:10 | amorphous | data for the syn component: 8.52 (m, 1H), 8.29 (d, 1H), 8.20 (br, 1H), 7.81 (d, 1H), 7.43 (d, 1H), 7.15 (t, 1H), 7.04 (d, 1H), 3.36 (m, 1H), 3.23 (m, 1H), 2.16 (t, 1H), 2.00 (m, 2H), 1.29 (m, 3H), 0.98 (m, 1H), 0.86 (m, 1H), 0.57 (m, 1H), 0.35 (m, 2H), −0.15 (m, 2H). |
| 29.208 syn:anti = 15:85 | amorphous | data for the anti component: 8.52 (m, 1H), 8.28 (d, 1H), 8.16 (br, 1H), 7.78 (d, 1H), 7.41 (d, 1H), 7.12 (t, 1H), 7.02 (d, 1H), 3.17 (m, 1H), 3.10 (m, 1H), 1.96 (m, 3H), 1.59 (m, 1H), 1.26-1.1 (m 4H), 0.91 (d, 6H). |
| 29.212 syn:anti = 47:53 | amorphous | data for the syn-anti mixture: 8.52 (m, 1H), 8.26 (m, 1H), 8.15 (br, 1H), 7.83 and 7.78 (two d, 1H), 7.42 (m, 1H), 7.17-7.10 (m, 1H), 7.04 (m, 1H), 3.37, 3.30, 3.27 and 3.23 (four m, 2H), 1.95 (m, 2H), 1.86 and 1.77 (two d, 1H), 1.45 (m, 1H), 1.38-1.10 (m, 6H), 0.85 and 0.74 (two t, 6H). |
| 29.214 syn:anti = 74:26 | amorphous | data for the syn component: 8.52 (m, 1H), 8.29 (d, 1H), 8.16 (br, 1H), 7.83 (d, 1H), 7.43 (d, 1H), 7.16 (t, 1H), 7.05 (d, 1H), 3.30 (m, 1H), 3.19 (m, 1H), 1.98 (m, 2H), 1.80-0.8 (m, 12H). |
| 29.218 syn:anti = 88:12 | amorphous | |

TABLE 30-continued

| Compound No. | m.p (/° C.) | NMR proton shifts (/ppm) (CDCl₃ unless otherwise stated) |
|---|---|---|
| 29.230 | amorphous | 8.53 (m, 1H), 8.29 (d, 1H), 8.17 (br, 1H), 7.71 (d, 1H), 7.43 (m, 1H), 7.13 (t, 1H), 7.06 (d, 1H), 3.91 (m, 1H), 3.82 (m, 1H), 1.93 (m, 2H), 1.63 (s, 6H), 1.40-1.23 (m, 2H). |
| 29.231 | amorphous | 8.53 (m, 1H), 8.26 (d, 1H), 8.16 (br, 1H), 7.73 (d, 1H), 7.43 (m, 1H), 7.13 (t, 1H), 7.05 (d, 1H), 3.91 (m, 1H), 3.81 (m, 1H), 2.1-1.89 (m, 6H), 1.40-1.23 (m, 2H), 0.93 (m, 6H). |

The compounds according to formula (I) may be prepared according to the following reaction schemes.

Preparation of a Compound of Formula (I)

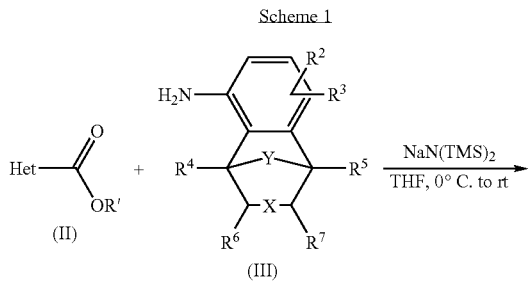

Scheme 1

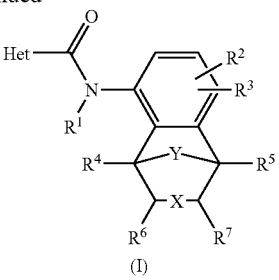

(I)

A compound of formula (I) [where $R^1$ is hydrogen; and Het, $R^2$, $R^3$, $R^4$, $R^5$, $R^6$, $R^7$, X and Y are as defined above for a compound of formula (I)] may be synthesized by reacting a compound of (II) [where Het is as defined above for a compound of formula (I) and R' is $C_{1-5}$ alkyl] with an aniline of formula (III) [where $R^2$, $R^3$, $R^4$, $R^5$, $R^6$, $R^7$, X and Y are as defined above for a compound of formula (I)] in the presence of NaN(TMS)₂ at −10° C. to ambient temperature, preferably in dry THF, as described by J. Wang et al. *Synlett,* 2001, 1485.

Scheme 2

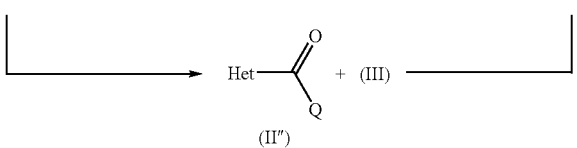

Alternatively, a compound of formula (I) [where R¹ is hydrogen; and Het, R², R³, R⁴, R⁵, R⁶, R⁷, X and Y are as defined above for a compound of formula (I)] may be prepared by reacting a compound of formula (II') [where Het is as defined above for a compound of formula (I)] with an aniline of formula (III) [where R², R³, R⁴, R⁵, R⁶, R⁷, X and Y are as defined above for a compound of formula (I)] in the presence of an activating agent [such as BOP—Cl] and two equivalents of a base [such as triethylamine] or by reacting a compound of formula (II') [where Het is as defined above for a compound of formula (I); and Q is Cl, F or Br] which is obtained from a compound of formula (II') by treatment with a halogenating agent such as thionyl chloride, oxalyl chloride, phosgene, SF₄, DAST, Deoxofluor or thionylbromide, with an aniline of formula (III) [where R², R³, R⁴, R⁵, R⁶, R⁷, X and Y are as defined above for a compound of formula (I)] in the presence of one equivalent of base [such as NEt₃, NaHCO₃, KHCO₃, Na₂CO₃ or K₂CO₃] in a solvent [such as dichloromethane, ethyl acetate or DMF] preferably at −10 to 30° C.

Scheme 3

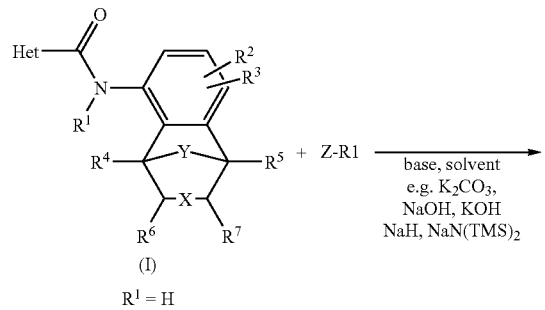

Furthermore a compound of formula (I) [where R¹ is hydrogen; and Het, R² to R⁷, X and Y are as defined for a compound of formula (I)] is reacted with a species Z—R¹ [where R¹ is as defined for formula (I), except that it is not hydrogen; and Z is preferably Cl, Br or I; or Z is such that Z—R¹ is an anhydride, that is, when R¹ is COR*, Z is OCOR*] in the presence of a base [for example NaH, NEt₃, NaHCO₃ or K₂CO₃] in an appropriate solvent [such as ethyl acetate] or in a biphasic mixture [such as dichloromethane/water mixture], at −10 to 30° C.

Starting Materials

Heterocyclic acids and esters [that is, compounds of formula (II') or (II)] are generally known from the literature or may be synthesized according to known methods.

Ortho-substituted aminobenzonorbonenes (including homologues) of formula (C) or (D) (scheme 4) may be accomplished through Diels-Alder addition of an in situ generated benzyne [for example starting from a 6-nitroanthranilic acid of formula (A), as described by L. Paquette et al, *J. Amer.* *Chem. Soc.* 99, 3734 (1977) or from other suitable precursers (see H. Pellissier et al. *Tetrahedron*, 59, 701 (2003)] to a 5-7 membered cyclic 1,4-diene to give a nitro-benzonorbornadiene of formula (B) according to or by analogy to L. Paquette et al, *J. Amer. Chem. Soc.* 99, 3734 (1977), D. Gravel et al. *Can. J. Chem.* 69, 1193 (1991), J. R. Malpass et al. *Tetrahedron*, 48, 861 (1992), D. E. Lewis et al. *Synthetic Communications*, 23, 993 (1993), R. N. Warrener et al. *Molecules*, 6, 353 (2001), R. N. Warrener et al. *Molecules*, 6, 194 (2001) or I. Fleming et al. *J. Chem. Soc., Perkin Trans.* 1, 2645 (1998). Suitable aprotic solvents for this step include ethyl acetate, dichloromethane, acetone, THF and dimethoxyethane. Reaction temperatures range from room temperature to 100° C., preferably 40-80° C.

Subsequent selective reduction of the nitro-group in a compound of formula (B) to give an amino-benzonorbornadiene of formula (C) requires mild conditions [for example, either metallic zinc in the presence of ammonium chloride, or aluminium amalgam]. Both methods work in protic solvents such as ethanol, water or mixtures thereof. Alternatively a compound of formula (C) may also be obtained from a compound of formula (B) by catalytic hydrogen reduction with a modified 5% Pt/C catalyst at elevated pressure (~10 bar) and elevated temperature (~100° C.) in toluene-water. Catalytic reduction under standard conditions (for example 5% Pd/C or 5% Ra/Ni or 5% Rh/C) in a solvent [such as methanol, ethanol, THF or ethyl acetate] reduces both the nitro-group and the double bond to furnish a benzonorbornene of formula (D). Preferred reaction conditions are ambient temperature and normal pressure.

Scheme 4

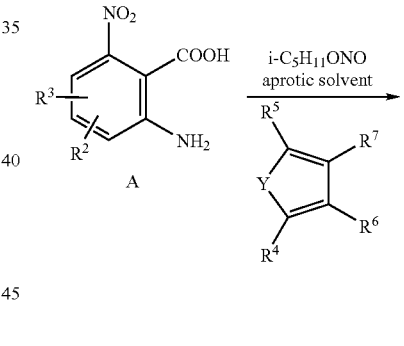

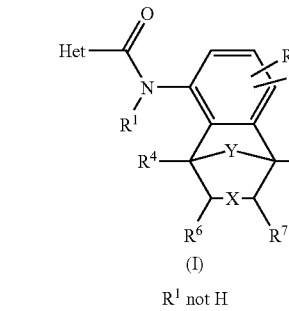

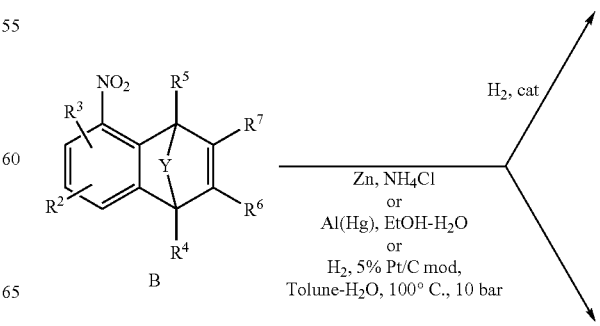

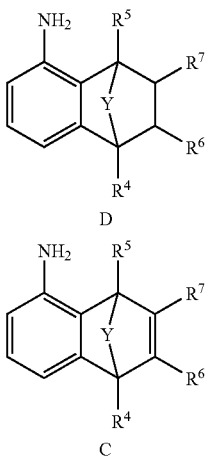

Some of the compounds of formulae (B), (C) and (D) are described in the literature [see, for example, L. A Paquette et al., *J. Amer. Chem. Soc.* 99, 3734 (1977); D. Gravel et al., *Canad. J. Chem.* 69, 1193 (1991); T. Nishiyama et al., *Rikagaku-hen,* 28, 37 (2000); H. Plieninger et al., *Chem. Ber.* 109, 2121 (1976); and A. J. Kirby et al., *J. Chem. Soc., Perkin Trans.* 2, 1997, 1081].

Novel starting materials of formulae (C) or (D) may be synthesized by analogy to scheme 4 or according to the literature cited above.

Surprisingly, it has now been found that the novel compounds of formula (I) have, for practical purposes, a very advantageous spectrum of activities for protecting plants against diseases that are caused by fungi as well as by bacteria and viruses.

The compounds of formula (I) can be used in the agricultural sector and related fields of use as active ingredients for controlling plant pests. The novel compounds are distinguished by excellent activity at low rates of application, by being well tolerated by plants and by being environmentally safe. They have very useful curative, preventive and systemic properties and are used for protecting numerous cultivated plants. The compounds of formula I can be used to inhibit or destroy the pests that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula (I) as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore the compounds according to present invention may be used for controlling fungi in related areas, for example in the protection of technical materials, including wood and wood related technical products, in food storage, in hygiene management, etc.

The compounds of formula (I) are, for example, effective against the phytopathogenic fungi of the following classes: Fungi imperfecti (e.g. *Botrytis, Pyricularia, Helminthosporium, Fusarium, Septoria, Cercospora* and *Alternaria*) and Basidiomycetes (e.g. *Rhizoctonia, Hemileia, Puccinia*). Additionally, they are also effective against the Ascomycetes classes (e.g. *Venturia* and *Erysiphe, Podosphaera, Monilinia, Uncinula*) and of the Oomycetes classes (e.g. *Phytophthora, Pythium, Plasmopara*). Outstanding activity has been observed against powdery mildew (*Erysiphe* spp.). Furthermore, the novel compounds of formula I are effective against phytopathogenic bacteria and viruses (e.g. against *Xanthomonas* spp, *Pseudomonas* spp, *Erwinia amylovora* as well as against the tobacco mosaic virus).

Within the scope of present invention, target crops to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamomum, camphor) or plants such as tobacco, nuts, coffee, eggplants, sugar cane, tea, pepper, vines, hops, bananas and natural rubber plants, as well as ornamentals.

The compounds of formula (I) are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO97/33890.

The compounds of formula (I) are normally used in the form of compositions and can be applied to the crop area or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula (I) can be mixed with other fungicides, resulting in some cases in unexpected synergistic activities. Mixing components which are particularly preferred are azoles, such as azaconazole, BAY 14120, bitertanol, bromuconazole, cyproconazole, difenoconazole, diniconazole, epoxiconazole, fenbuconazole, fluquinconazole, flusilazole, flutriafol, hexaconazole, imazalil, imibenconazole, ipconazole, metconazole, myclobutanil, pefurazoate, penconazole, pyrifenox, prochloraz, propiconazole, simeconazole, tebuconazole, tetraconazole, triadimefon, triadimenol, triflumizole, triticonazole; pyrimidinyl carbinole, such as ancymidol, fenarimol, nuarimol; 2-amino-pyrimidines, such as bupirimate, dimethirimol, ethirimol; morpholines, such as dodemorph, fenpropidine, fenpropimorph, spiroxamine, tridemorph; anilinopyrimidines, such as cyprodinil, mepanipyrim, pyrimethanil; pyrroles, such as fenpiclonil, fludioxonil; phenylamides, such as benalaxyl, furalaxyl, metalaxyl, R-metalaxyl, ofurace, oxadixyl; benzimidazoles, such as benomyl, carbendazim, debacarb, fuberidazole, thiabendazole; dicarboximides, such as chlozolinate, dichlozoline, iprodione, myclozoline, procymidone, vinclozoline; carboxamides, such as carboxin, fenfuram, flutolanil, mepronil, oxycarboxin, thifluzamide; guanidines, such as guazatine, dodine, iminoctadine; strobilurines, such as azoxystrobin, kresoxim-methyl, metominostrobin, SSF-129, trifloxystrobin, picoxystrobin, BAS 500F (proposed name pyraclostrobin), BAS 520; dithiocarbamates, such as ferbam, mancozeb, maneb, metiram, propineb, thiram, zineb, ziram; N-halomethylthiotetrahydrophthalimides, such as captafol, captan, dichlofluanid, fluoromides, folpet, tolyfluanid; Cu-compounds, such as Bordeaux mixture, copper hydroxide, copper oxychloride, copper sulfate, cuprous oxide, mancopper, oxine-copper; nitrophenol-derivatives, such as dinocap, nitrothal-isopropyl; organo-p-derivatives, such as edifenphos, iprobenphos, isoprothiolane, phosdiphen, pyrazophos, tolclofos-methyl; various others, such as acibenzolar-S-methyl, anilazine, benthiavalicarb, blasticidin-S, chinomethionate, chloroneb, chlorothalonil, cyflufenamid, cymoxanil, dichlone, diclomezine, dicloran, diethofencarb, dimethomorph, SYP-LI90 (proposed name: flumorph), dithianon, ethaboxam, etridiazole, famoxadone, fenamidone, fenoxanil, fentin, ferimzone, fluazinam, flusulfamide, fenhexamid, fosetyl-aluminium, hymexazol, iprovalicarb, IKF-916 (cyazofamid), kasugamycin, methasulfocarb, metrafenone, nicobifen, pencycuron, phthalide, polyoxins, probenazole, propamocarb, pyroquilon, quinoxyfen, quintozene, sulfur, triazoxide, tricyclazole, triforine, validamycin, zoxamide (RH7281).

A preferred method of applying a compound of formula (I), or an agrochemical composition which contains at least one of said compounds, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, for example in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation [that is, a composition containing the compound of formula (I)] and, if desired, a solid or liquid adjuvant, is prepared in a known manner, typically by intimately mixing and/or grinding the compound with extenders, for example solvents, solid carriers and, optionally, surface active compounds (surfactants).

The agrochemical formulations will usually contain from 0.1 to 99% by weight, preferably from 0.1 to 95% by weight, of the compound of formula I 99.9 to 1% by weight, preferably 99.8 to 5% by weight, of a solid or liquid adjuvant, and from 0 to 25% by weight, preferably from 0.1 to 25% by weight, of a surfactant.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

Whereas it is preferred to formulate commercial products as concentrates, the end user will normally use dilute formulations.

The following non-limiting Examples illustrate the above-described invention in more detail.

Example 1

This Example illustrates the preparation of Compound No. 2.01.

A solution of 1,4-dimethyl-5-nitro-1,4-dihydro-1,4-epoxynaphthalene (5.49 g; 25.27 mmol) (see T. Nishiyama et al., *Rikagaku-hen*, 28, 37-43 (2000)) in THF (55 ml) was hydrogenated in the presence of RaNi (1.1 g) at ambient temperature. Hydrogen uptake was 2.23 liters (97%) after 18 hours. After filtering off the catalyst the filtrate was evaporated and taken up into ether, washed with an aqueous $NaHCO_3$-solution and dried ($NaSO_4$) to give 4.60 g of crude product as an oil. Trituration with hexane and a trace of ether furnished a total of 4.51 g (94%) of reddish crystalline product.

Example 2

This Example illustrates the preparation of Compound No. 1.01.

To 1,4-dimethyl-5-nitro-1,4-dihydro-1,4-epoxynaphthalene (4.22 g; 19.43 mmol) (see Example 1) in ethanol (60 ml) was added a solution of ammoniumchloride (2.08 g) in water (5.2 ml) at 47° C. Under vigorous stirring, zinc powder (9.10 g; 0.14 mol) was added in portions over a period of 5 minutes. The suspension was heated to reflux for 5½ hours followed by filtration through Hyflo™ to give a clear yellow filtrate. After evaporation the crude product amounted 4.57 g of a viscous oil. Column chromatography on silica gel in ethyl acetate-hexane (1:4) gave 1.24 g (34%) of the desired product as brownish crystals.

Example 3

This Example illustrates the preparation of Compound No. 2.16.

A solution of 5-nitrobenzonorbornadiene (L. A. Paquette et al., *J. Amer. Chem. Soc.* 99, 3734 (1977)) (2.52 g; 13.46 mmol) in methanol (100 ml) was hydrogenated in the presence of 5% Pd/C (0.5 g) at ambient temperature. $H_2$-uptake was 1.14 liters (95%) after 11 minutes. The solution was filtered from the catalyst and evaporated to give pure product (1.86 g; 87%) as a yellow oil, which solidified on standing at room temperature (m.p. 63-64° C.).

Example 4

This Example illustrates the preparation of Compound No. 3.023.

A solution of 1-methyl-4-trifluoromethyl-1H-pyrrole-3-carboxylic acid (1.02 g; 5.3 mmol) and a catalytic amount of DMF (3 drops) in dichloromethane (20 ml) was reacted under initial ice cooling with oxalyl chloride (0.805 g; 1.2 eq.) for 2 hours. Within 15 minutes, the reaction mixture was then added dropwise to a solution of 1,8-dimethyl-11-oxa-tricyclo [6.2.1.0*2,7*]undeca-2,4,6-trien-3-ylamine (Compound No. 2.01; see preparation above) (1.0 g; 5.284 mmol) and triethylamine (1.07 g; 10.57 mmol) in 20 ml dichloromethane under cooling (3-7° C.) with subsequent stirring at ambient temperature for 3¼ hours. The reaction mixture was then poured on to ice water and extracted with dichloromethane to give 2.26 g of crude product. Purification on silica gel in ethyl acetate-hexane (1:1) followed by trituration with ether-hexane furnished a solid (1.14 g; 59%) as a mixture of isomers.

Example 5

This Example illustrates the preparation of Compound No. 3.024.

A suspension of NaH (0.107 g; 60% oil dispersion, ~2.7 mmol) in DMF (5 ml) was reacted with a solution of 1-methyl-4-trifluoromethyl-1H-pyrrole-3-carboxylic acid(1,8-dimethyl-11-oxa-tricyclo[6.2.1.0*2,7*]undeca-2,4,6-trien-3-yl)-amide (Compound No. 3.023; see preparation above) (0.65 g; 1.784 mmol) in 5 ml DMF at 10-15° C. for 30 minutes. 3-Bromo-1-propyne (0.276 g; 2.32 mmol) was added and the mixture was further reacted overnight at ambient temperature. After aqueous work up with ice water and ethyl acetate and purification on silica gel 0.36 g (50%) of the desired product as a mixture of isomers were obtained.

Formulation Examples for Compounds of Formula (I)

Working procedures for preparing formulations of the compounds of formula I such as Emulsifiable Concentrates, Solutions, Granules, Dusts and Wettable Powders are described in WO97/33890.

Biological Examples

Fungicidal Actions

Example B-1

Action Against *Puccinia recondita*/Wheat (Brownrust on Wheat)

1 week old wheat plants cv. Arina are treated with the formulated test compound (0.02% active ingredient) in a spray chamber. One day after application, the wheat plants are inoculated by spraying a spore suspension ($1 \times 10^5$ uredospores/ml) on the test plants. After an incubation period of 2 days at 20° C. and 95% r.h. the plants are kept in a greenhouse for 8 days at 20° C. and 60% r.h. The disease incidence is assessed 10 days after inoculation.

Infestation is prevented virtually completely (0-5% infestation) with each of Compounds 3.048, 14.048, 29.048, 15.048, 20.048, 3.028, 22.048, 21.048, 15.023, 15.027, 15.028, 3.035, 14.035, 15.035, 15.052, 14.210, 15.210, 14.202 and 15.202.

Example B-2

Action Against *Podosphaera leucotricha*/Apple (Powdery Mildew on Apple)

5 week old apple seedlings cv. McIntosh are treated with the formulated test compound (0.02% active ingredient) in a spray chamber. One day after, the application apple plants are inoculated by shaking plants infected with apple powdery mildew above the test plants. After an incubation period of 12 days at 22° C. and 60% r.h. under a light regime of 14/10 hours (light/dark) the disease incidence is assessed.

Compounds 3.048, 14.048, 15.048, 22.048, 14.210, 15.210, 14.202, 15.202 and 15.023 each exhibit strong efficacy (<20% infestation).

Example B-3

Action Against *Venturia inaequalis*/Apple (Scab on Apple)

4 week old apple seedlings cv. McIntosh are treated with the formulated test compound (0.02% active ingredient) in a spray chamber. One day after application, the apple plants are inoculated by spraying a spore suspension ($4 \times 10^5$ conidia/ml) on the test plants. After an incubation period of 4 days at 21° C. and 95% r.h. the plants are placed for 4 days at 21° C. and 60% r.h. in a greenhouse. After another 4 day incubation period at 21° C. and 95% r.h. the disease incidence is assessed.

Compounds 3.048, 14.048, 14.210, 15.210, 14.202, 15.202 and 15.048 each exhibit strong efficacy (<20% infestation).

Example B-4

Action Against *Erysiphe graminis*/Barley (Powdery Mildew on Barley)

1 week old barley plants cv. Regina are treated with the formulated test compound (0.02% active ingredient) in a spray chamber. One day after application, the barley plants are inoculated by shaking powdery mildew infected plants above the test plants. After an incubation period of 6 days at 20° C./18° C. (day/night) and 60% r.h. in a greenhouse the disease incidence is assessed.

Compounds 3.023, 14.023, 3.048, 14.048, 15.048, 3.027, 3.028, 15.023, 14.210, 15.210, 14.202, 15.202 and 15.027 each exhibit strong efficacy (<20% infestation).

Example B-5

Action Against *Botrytis cinerea*/Grape (Botrytis on Grapes)

5 week old grape seedlings cv. Gutedel are treated with the formulated test compound (0.02% active ingredient) in a spray chamber. Two days after application, the grape plants are inoculated by spraying a spore suspension ($1 \times 10^6$ conidia/ml) on the test plants. After an incubation period of 4 days at 21° C. and 95% r.h. in a greenhouse the disease incidence is assessed.

Compounds 14.048, 15.048, 3.028, 14.210, 15.210, 14.202, 15.202 and 15.027 each show good activity in this test (<50% disease incidence).

Example B-6

Action Against *Botrytis cinerea*/Tomato (Botrytis on Tomatoes)

4 week old tomato plants cv. Roter Gnom are treated with the formulated test compound (0.02% active ingredient) in a spray chamber. Two days after application, the tomato plants are inoculated by spraying a spore suspension ($1 \times 10^5$ conidia/ml) on the test plants. After an incubation period of 4 days at 20° C. and 95% r.h. in a growth chamber the disease incidence is assessed.

Compounds 3.048, 3.052, 14.052, 15.048, 14.210, 15.210, 14.202, 15.202 and 15.023 each exhibit good efficacy (<50% disease incidence).

Example B-7

Action Against *Septoria nodorum*/Wheat (Septoria Leaf Spot on Wheat)

1 week old wheat plants cv. Arina are treated with the formulated test compound (0.02% active ingredient) in a spray chamber. One day after application, the wheat plants are inoculated by spraying a spore suspension ($5 \times 10^5$ conidia/ml) on the test plants. After an incubation period of 1 day at 20° C. and 95% r.h. the plants are kept for 10 days at 20° C. and 60% r.h. in a greenhouse. The disease incidence is assessed 11 days after inoculation.

Compounds 3.002, 3.048, 14.048, 14.210, 15.210, 14.202, 15.202 and 15.048 each show good activity in this test (<50% disease incidence).

Example B-8

Action Against *Helminthosporium teres*/Barley (Net Blotch on Barley)

1 week old barley plants cv. Regina are treated with the formulated test compound (0.02% active ingredient) in a spray chamber. Two days after application, the barley plants are inoculated by spraying a spore suspension ($3 \times 10^4$ conidia/ml) on the test plants. After an incubation period of 4 days at 20° C. and 95% r.h. in a greenhouse the disease incidence is assessed.

Compounds 3.023, 14.023, 3.048, 14.048, 15.048, 3.027, 15.023, 15.027, 14.210, 15.210, 14.202, 15.202 and 15.028 each show good activity in this test (<20% disease incidence).

Example B-9

Action Against *Alternaria solani*/Tomato (Early Blight on Tomatoes)

4 week old tomato plants cv. Roter Gnom are treated with the formulated test compound (0.02% active ingredient) in a spray chamber. Two days after application, the tomato plants are inoculated by spraying a spore suspension ($2 \times 10^5$ conidia/ml) on the test plants. After an incubation period of 3 days at 20° C. and 95% r.h. in a growth chamber the disease incidence is assessed.

Compounds 3.023, 14.023, 3.048, 14.048, 14.210, 15.210, 14.202, 15.202 and 15.048 each show good activity in this test (<20% disease incidence).

Example B-10

Action Against *Uncinula necator*/Grape (Powdery Mildew on Grapes)

5 week old grape seedlings cv. Gutedel are treated with the formulated test compound (0.02% active ingredient) in a spray chamber. One day after application, the grape plants are inoculated by shaking plants infected with grape powdery mildew above the test plants. After an incubation period of 7 days at 26° C. and 60% r.h. under a light regime of 14/10 hours (light/dark) the disease incidence is assessed.

Compounds 14.048, 15.048, 14.028 and 15.023 each show good activity in this test (<20% disease incidence).

Example B-11

Systemic Action Against *Erysiphe graminis*/Barley (Powdery Mildew on Barley) (Pouch Test)

The formulated test compound (0.002% active ingredient) is applied into a pouch which was previously equipped with a filter paper. After the application barley seeds (cv. Express) are sown into the upper fault of the filter paper. The prepared pouches are then incubated at 23° C./18° C. (day/night) and 80% r.h. One week after sowing barley plants were inoculated by shaking powdery mildew infected plants above the test plants. After an incubation period of 6 days the disease incidence was assessed. The efficacy of each test compound is used as an indicator for systemic activity.

Compounds 14.024, 3.002, 3.048, 29.048, 3.027, 22.048, 21.048, 15.023, 15.027, 15.028 and 15.035 each show good activity in this test (<50% disease incidence).

Example B-12

Action Against *Fusarium culmorum*/Wheat (Fusarium Head Blight on Wheat) (Pouch Test)

A conidia suspension of *F. culmorum* ($7 \times 10^5$ conidia/ml) is mixed with the formulated test compound (0.002% active ingredient). The mixture is applied into a pouch which was previously equipped with a filter paper. After the application wheat seeds (cv. Orestis) are sown into the upper fault of the filter paper. The prepared pouches are then incubated for II days at ca. 10-18° C. and 100% r.h. with a daily light period of 14 hours. The evaluation is made by assessing the degree of disease occurrence in the form of brown lesions on the roots.

Compounds 14.024, 15.048, 20.048, 14.027, 24.048 and 3.035 each show good activity in this test (<50% disease incidence).

Example B-13

Action *Gaeumannomyces graminis*/Wheat (Take-all on Wheat) (Pouch Test)

A defined amount of mycelium of *G. graminis* is mixed with water. The formulated test compound (0.002% active ingredient) is added to the mycelium suspension. The mixture is applied into a pouch which was previously equipped with a filter paper. After the application wheat seeds (cv. Orestis) are sown into the upper fault of the filter paper. The prepared pouches are then incubated for 14 days at 18° C./16° C. (day/night) and 80% r.h. with a daily light period of 14 hours. The evaluation is made by assessing the degree of root browning.

Compounds 15.048, 20.048, 21.048, 15.028 and 15.052 each show good activity in this test (<50% disease incidence).

Example B-14

Action Against *Puccinia recondita*/Wheat (Brownrust on Wheat) (Pouch Test)

Formulated test compound (0.002% active ingredient) is applied into a pouch which was previously equipped with a filter paper. After the application wheat seeds (cv. Arina) are sown into the upper fault of the filter paper. The prepared pouches are then incubated at 23° C./18° C. (day/night) and 80% r.h. One week after sowing, the wheat plants were inoculated by spraying a spore suspension (1×10⁵ uredospores/ml) on the test plants. After an incubation period of 1 day at 23° C. and 95% r.h. the plants were kept for 9 days at 20° C./18° C. (day/night) and 80% r.h. The disease incidence was assessed 10 days after inoculation. The efficacy of each test compound is used as an indicator for systemic activity.

Compounds 14.024, 3.002, 14.002, 15.048, 20.048, 3.027, 22.048, 15.023, 15.027, 15.028, 3.035, 14.035 and 15.035 each show good activity in this test (<50% disease incidence).

Example B-15

Action Against *Rhizoctonia solani*/Rice (Sheath Blight on Rice) (Pouch Test)

A defined amount of mycelium of *R. solani* is mixed with water. The formulated test compound (0.002% active ingredient) is added to the mycelium suspension. The mixture is applied into a pouch which was previously equipped with a filter paper. After the application rice seeds (cv. Koshihikari) are sown into the upper fault of the filter paper. The prepared pouches are then incubated for 10 days at 23° C./21° C. (day/night) and 100% r.h. with a daily light period of 14 hours. The evaluation is made by assessing the degree of disease occurrence in the form of brown lesions on the roots.

Compounds 3.048, 14.048, 29.048, 3.052, 29.052, 14.052, 15.048, 20.048, 3.027, 14.028, 22.048, 21.048, 4.048, 15.023, 3.035, 14.035 and 15.035 each show good activity in this test (<50% disease incidence).

Example B-16

Action Against *Septoria nodorum*/Wheat (Septoria Leaf Spot on Wheat) (Pouch Test)

The formulated test compound (0.002% active ingredient) was applied into a pouch which was previously equipped with a filter paper. After the application, wheat seeds (cv. Arina) were sown into the upper fault of the filter paper. The prepared pouches were then incubated at 23° C./18° C. (day/night) and 80% r.h. One week after sowing, the wheat plants were inoculated by spraying a spore suspension (5×10⁵ conidia/ml) on the test plants. After an incubation period of 1 day at 23° C. and 95% r.h. the plants were kept for 9 days at 20° C./18° C. (day/night) and 80% r.h. The disease incidence was assessed 8 days after inoculation. The efficacy of each test compound is used as an indicator for systemic activity.

Compounds 3.048, 29.048, 15.048, 14.027, 15.023 and 15.027 each show good activity in this test (<50% disease incidence).

Example B-17

Action Against *Septoria tritici*/Wheat (Septoria Leaf Spot on Wheat)

2 week old wheat plants cv. Riband are treated with the formulated test compound (0.02% active ingredient) in a spray chamber. One day after application, wheat plants are inoculated by spraying a spore suspension (10×10⁵ conidia/ml) on the test plants. After an incubation period of 1 day at 23° C. and 95% r.h., the plants are kept for 16 days at 23° C. and 60% r.h. in a greenhouse. The disease incidence is assessed 18 days after inoculation.

Compounds 14.202 or 14.210 each show good activity in this test (<20% disease incidence).

The invention claimed is:

1. A compound of formula (I):

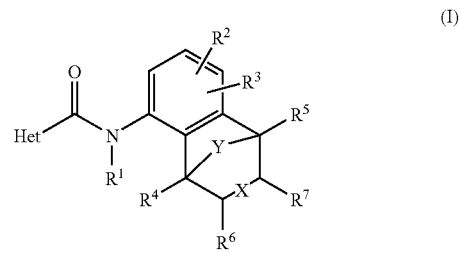

where Het is a 5- or 6-membered heterocyclic ring containing one to three heteroatoms, each independently selected from oxygen, nitrogen and sulphur, provided that the ring is not 1,2,3-triazole, the ring being substituted by groups $R^8$, $R^9$ and $R^{10}$; X is a single or double bond; Y is O, S, $N(R^{11})$ or $(CR^{12}R^{13})(CR^{14}R^{15})_m(CR^{16}R^{17})_n$; m is 0 or 1; n is 0 or 1; $R^1$ is hydrogen, $C_{1-4}$ alkyl, $C_{1-4}$ haloalkyl, $C_{1-4}$ alkoxy, $C_{1-4}$ haloalkoxy, $CH_2C\equiv CR^{18}$, $CH_2CR^{19}=CHR^{20}$, $CH=C=CH_2$ or $COR^{21}$; $R^2$ and $R^3$ are each, independently, hydrogen, halogen, $C_{1-4}$ alkyl, $C_{1-4}$ alkoxy or $C_{1-4}$ haloalkoxy; $R^4$, $R^5$, $R^6$ and $R^7$ are each, independently, hydrogen, halogen, $C_{1-4}$ alkyl, $C_{1-4}$ haloalkyl, $C_{1-4}$ alkoxy, $C_{1-4}$ haloalkoxy, $C_{1-4}$ alkylthio, $C_{1-4}$ haloalkylthio, hydroxymethyl, $C_{1-4}$ alkoxymethyl, $C(O)CH_3$ or $C(O)OCH_3$; $R^8$, $R^9$ and $R^{10}$ are each, independently, hydrogen, halogen, cyano, nitro, $C_{1-4}$ alkyl, $C_{1-4}$ haloalkyl, $C_{1-4}$ alkoxy$(C_{1-4})$alkylene or $C_{1-4}$ haloalkoxy$(C_{1-4})$alkylene, provided that at least one of $R^8$, $R^9$ and $R^{10}$ is not hydrogen; $R^{11}$ is hydrogen, $C_{1-4}$ alkyl, benzyl optionally substituted with up to three ring substituents with each ring substituent independently selected from halogen or $C_{1-4}$ alkyl or $C_{1-4}$ haloalkyl or $C_{1-4}$ alkoxy, formyl, $C(O)C_{1-4}$ alkyl optionally substituted by halogen or $C_{1-4}$ alkoxy, $C(=O)O-C_{1-6}$ alkyl optionally substituted by halogen, $C_{1-4}$ alkoxy or cyano, or $C_{1-4}$ alkoxy$(C_{1-4})$alkylene; $R^{12}$, $R^{13}$, $R^{14}$, $R^{15}$, $R^{16}$ and $R^{17}$ are each, independently, hydrogen, halogen, hydroxy, $C_{1-6}$ alkyl, $C_{2-6}$ alkenyl, a 3-7 membered saturated ring optionally substituted by up to three methyl groups and optionally containing one heteroatom selected from nitrogen and oxygen, or $C_{1-4}$ alkoxy, wherein each of $C_{1-6}$ alkyl and $C_{2-6}$ alkenyl may independently be optionally substituted by halogen, hydroxy, $C_{1-4}$ alkoxy, =O, aryl or $O-C(O)-C_{1-4}$ alkyl or a 3-7 membered carboxylic ring optionally substituted by up to three methyl groups; or $R^{12}$ and $R^{13}$ together with the carbon atom to which they are attached form the group C=O or a 3-5 membered carbocyclic ring optionally substituted by up to three methyl groups and optionally with up to 2 heteroatoms each independently selected from O and N; or $R^{12}$ and $R^{13}$ together form a $C_{1-6}$ alkylidene optionally substituted by up to three methyl groups or a $C_{3-6}$ cycloalkylidene group optionally substituted by up to three methyl groups; $R^{18}$, $R^{19}$ and $R^{20}$ are each, independently, hydrogen, halogen, $C_{1-4}$ alkyl, $C_{1-4}$ haloalkyl or $C_{1-4}$ alkoxy$(C_{1-4})$alkylene; and $R^{21}$ is hydrogen, $C_{1-6}$ alkyl, $C_{1-6}$ haloalkyl, $C_{1-4}$ alkoxy$(C_{1-4})$alkylene, $C_{1-4}$ alkyl-S-$(C_{1-4})$alkylene, $C_{1-4}$ alkoxy or aryl.

2. A compound of claim 1, where Het is pyrrolyl, pyrazolyl, thiazolyl, oxazolyl, pyridinyl, pyrimidyl, pyridazinyl, 2,3-dihydro-[1,4]oxathiine-6-yl, oxazinyl, thiazinyl or triazinyl.

3. A compound of claim 1, where Y is O, $N(R^{11})$ or $(CR^{12}R^{13})(CR^{14}R^{15})_m(CR^{16}R^{17})_n$.

4. A compound of claim 1, where $R^1$ is hydrogen, $CH_2C=CR^{18}$, $CH=C=CH_2$ or $COR^{21}$.

5. A compound of claim 1, where $R^2$ is hydrogen, halogen or $C_{1-4}$ alkyl.

6. A compound of claim 1, where $R^3$ is hydrogen or methyl.

7. A composition for controlling microorganisms and infestation of plants therewith, wherein the active ingredient is the compound of claim 1 together with a suitable carrier.

8. A compound of claim 1, where Het is pyrazolyl and $R^8$, $R^9$ and $R^{10}$ comprise hydrogen, $C_{1-4}$ alkyl and $C_{1-4}$ haloalkyl respectively.

9. A compound of claim 8, where $C_{1-4}$ alkyl comprises methyl, and $C_{1-4}$ haloalkyl comprises $CHF_2$.

10. A compound of claim 9, where each of $R^1$, $R^2$, $R^3$, $R^4$, $R^5$, $R^6$ and $R^7$ is independently hydrogen.

11. A compound of claim 10, where X is a double bond.

12. A compound of claim 11, where Y is $(CR^{12}R^{13})$.

13. A compound of claim 12, where $R^{12}$ comprises hydrogen, and $R^{13}$ comprises $i-C_3H_7$.

14. A compound of formula (I):

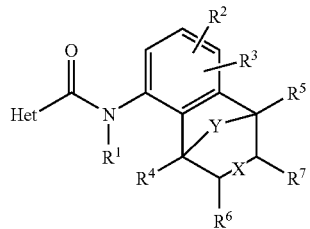

(I)

where Het is pyrrolyl or pyrazolyl substituted by groups $R^8$, $R^9$ and $R^{10}$; X is a single or double bond; Y is $(CR^{12}R^{13})(CR^{14}R^{15})_m(CR^{16}R^{17})_n$; m is 0 or 1; n is 0 or 1; $R^1$, $R^2$ and $R^3$ are each independently hydrogen; $R^4$, $R^5$, $R^6$ and $R^7$ are each, independently, hydrogen or methyl; $R^8$, $R^9$ and $R^{10}$ are each, independently, hydrogen, chloro, fluoro, methyl, $CF_3$, $CHF_2$ or $CH_2F$, provided that at least one of $R^8$, $R^9$ and $R^{10}$ is not hydrogen; $R^{12}$ and $R^{13}$ are each, independently, hydrogen, halogen, $C_{1-5}$ alkyl, $C_{1-3}$ alkoxy, $CH_2OH$, $CH(O)$, $C_{3-6}$ cycloalkyl, $CH_2O-C(=O)CH_3$, $CH_2-C_{3-6}$ cycloalkyl or benzyl; or $R^{12}$ and $R^{13}$ together with the carbon atom to which they are attached form the group $C=O$ or a 3-5 membered carbocyclic ring; or $R^{12}$ and $R^{13}$ together form $C_{1-5}$ alkylidene or $C_{3-6}$ cycloalkylidene.

15. A compound of claim 14, where Het is pyrazolyl and $R^8$, $R^9$ and $R^{10}$ comprise hydrogen, methyl, and $CHF_2$ respectively.

16. A compound of claim 15, where each of $R^1$, $R^2$, $R^3$, $R^4$, $R^5$, $R^6$ and $R^7$ is independently hydrogen.

17. A compound of claim 16, where X is a double bond, and Y is $(CR^{12}R^{13})$.

18. A compound of claim 17, where $R^{12}$ and $R^{13}$ are each, independently, H, $CH_3$, $C_2H_5$, $n-C_3H_7$, $i-C_3H_7$, $n-C_4H_9$, $sec-C_4H_9$, $i-C_4H_9$, $CH(C_2H_5)_2$, $CH_2$-cyclopropyl or cyclopentyl; or $R^{12}$ and $R^{13}$ together with the carbon atom to which they are attached form a 3-membered or 5-membered carbocyclic ring.

19. A compound of claim 18, where $R^{12}$ comprises hydrogen, and $R^{13}$ comprises $i-C_3H_7$.

20. A method of controlling infestation of cultivated plants by phytopathogenic microorganisms by application of the compound of claim 1 to plants, to parts thereof or the locus thereof.

* * * * *